US011316115B2

(12) United States Patent
Zhang et al.

(10) Patent No.: US 11,316,115 B2
(45) Date of Patent: Apr. 26, 2022

(54) ORGANIC COMPOUND, DISPLAY PANEL AND DISPLAY DEVICE

(71) Applicant: WUHAN TIANMA MICRO-ELECTRONICS CO., LTD., Wuhan (CN)

(72) Inventors: Lei Zhang, Wuhan (CN); Wei Gao, Wuhan (CN); Jinghua Niu, Wuhan (CN); Wenpeng Dai, Wuhan (CN); Ping An, Wuhan (CN)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 384 days.

(21) Appl. No.: 16/502,408

(22) Filed: Jul. 3, 2019

(65) Prior Publication Data

US 2020/0203626 A1 Jun. 25, 2020

(30) Foreign Application Priority Data

Dec. 24, 2018 (CN) ......................... 201811581250.3

(51) Int. Cl.
*C07D 471/04* (2006.01)
*C09K 11/06* (2006.01)
(Continued)

(52) U.S. Cl.
CPC ........ *H01L 51/0072* (2013.01); *C07D 471/04* (2013.01); *C09K 11/06* (2013.01);
(Continued)

(58) Field of Classification Search
CPC .......................... C07D 471/04; H01L 51/0072
See application file for complete search history.

(56) References Cited

U.S. PATENT DOCUMENTS 7,834,346 B2 * 11/2010 Hosokawa ........... C07D 471/04 257/40
2015/0041773 A1 * 2/2015 Park .................... H01L 51/0067 257/40
2016/0240794 A1 * 8/2016 Yamada ............. H01L 51/0072

FOREIGN PATENT DOCUMENTS

CN 107548399 A 1/2018
CN 108218858 A 6/2018
(Continued)

OTHER PUBLICATIONS

Moon et al., https://spie.org/news/5197-transparent-organic-leds-for-new-lighting-applications?SSO=1 (Year: 2013).*

*Primary Examiner* — Vu A Nguyen
(74) *Attorney, Agent, or Firm* — Alston & Bird LLP

(57) ABSTRACT

An organic compound, a display panel, and a display apparatus are provided. The organic compound has a structure represented by Chemical Formula 1, in which $R_1$ to $R_8$ are each independently selected from hydrogen, substituted or unsubstituted C6-C18 aryl, pyridyl, quinolyl, C1-C16 alkyl, C1-C16 alkoxy, hydroxyl, and carboxyl; m, n, x and y each independently represent 0 or 1, where m+x≥1, n+y≥1, m+n≥1, and x+y≥1; $L_1$ and $L_2$ are each independently selected from substituted or unsubstituted C6-C30 arylene, substituted or unsubstituted C5-C30 heteroarylene, substituted or unsubstituted C1-C8 alkylene, and substituted or
(Continued)

unsubstituted C1-C8 alkyleneoxy; Ar1 and Ar2 each independently have a structure shown in Chemical Formula 2, in which $R_{21}$ to $R_{27}$ are each independently selected from hydrogen, substituted or unsubstituted C6-C18 aryl, pyridyl, quinolyl, C1-C16 alkyl, C1-C16 alkoxy, hydroxyl, and carboxyl.

Chemical Formula 1

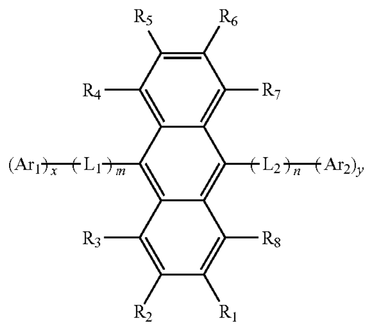

9 Claims, 2 Drawing Sheets

(51) Int. Cl.
*H01L 51/00* (2006.01)
*H01L 51/50* (2006.01)
*H01L 51/52* (2006.01)

(52) U.S. Cl.
CPC ...... *H01L 51/0052* (2013.01); *H01L 51/0067* (2013.01); *C09K 2211/1018* (2013.01); *H01L 51/5012* (2013.01); *H01L 51/5056* (2013.01); *H01L 51/5072* (2013.01); *H01L 51/5092* (2013.01); *H01L 51/5253* (2013.01); *H01L 2251/552* (2013.01)

(56) References Cited

FOREIGN PATENT DOCUMENTS

| | | | |
|---|---|---|---|
| KR | 20190051714 | A | 5/2019 |
| KR | 20190053606 | A | 5/2019 |
| WO | 2018124588 | A1 | 7/2018 |

* cited by examiner

ORGANIC COMPOUND, DISPLAY PANEL AND DISPLAY DEVICE

CROSS-REFERENCE TO RELATED APPLICATIONS

The present application claims priority to Chinese Patent Application No. CN 201811581250.3, filed on Dec. 24, 2018, the content of which is incorporated herein by reference in its entirety.

TECHNICAL FIELD

The present disclosure relates to the field of organic electroluminescent materials, and in particular, to a novel organic compound containing anthryl and phenanthrolinyl group, and a display panel containing the organic compound and a display apparatus including the display panel.

BACKGROUND

For the commercial and practical applications of electroluminescent devices, it is desirable to obtain electronic transmission materials with higher transmission efficiency and better application performance. Researchers have made exploratory efforts in this field. The electron transmission material used in a conventional electroluminescent device is Alq3 (8-hydroxyquinoline aluminum), but the electron mobility of Alq3 is relatively low (about $10^{-6}$ $cm^2/Vs$), which causes imbalance of the electron transmission and hole transmission of the device.

At present, the commonly used electron transmission materials, such as batho-phenanthroline (BPhen), bathocuproine (BCP), and TmPyPB (1,3,5-tri[(3-pyridyl)-3)-phenyl]benzene)), basically meet the market's demands for organic electroluminescent panels, but their glass transition temperature is low (generally less than 85° C.). The Joule heat generated during the operation of the devices using such materials may lead to molecular degradation and molecular structure changes, which results in low efficiency and poor thermal stability of the devices. Meanwhile, these materials have symmetric and regular molecular structures and thus easily crystallize after a long time. Once the electron transmission material crystallizes, the charge transition mechanism of the crystallized molecules will be different from the amorphous film mechanism of these molecules during the normal operation, resulting in deterioration in the performance of electron transmission and an imbalance between electron mobility and hole mobility of the whole device. In addition, the exciton formation efficiency is greatly reduced, and the excitons enrich at the interface between the electron transmission layer and the light-emitting layer, resulting in a significant drop in device efficiency and lifetime.

SUMMARY

The present disclosure is to provide a novel organic compound containing anthryl and phenanthrolinyl, and a display panel containing the organic compound and a display apparatus including the display panel. The organic compound can be used as a stable and efficient electron transmission material and/or electron injection material, can simultaneously have high electron mobility and high glass transition temperature, and can be effectively doped, which can reduce the threshold voltage, improve device efficiency, and extend service life of the device. Therefore, the compound of the present disclosure has an important practical application value.

In an aspect, the present disclosure provides organic compound, having a structure represented by Chemical Formula 1:

Chemical Formula 1

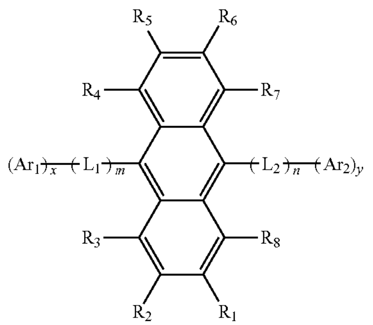

wherein $R_1$ to $R_8$ are each independently selected from hydrogen, substituted or unsubstituted C6-C18 aryl, substituted or unsubstituted pyridyl, substituted or unsubstituted quinolyl, substituted or unsubstituted C1-C16 alkyl, substituted or unsubstituted C1-C16 alkoxy, hydroxyl, and carboxyl;

m, n, x and y each independently represent 0 or 1, where $m+x\geq1$, $n+y\geq1$, $m+n\geq1$, and $x+y\geq1$;

$L_1$ and $L_2$ are each independently selected from substituted or unsubstituted C6-C30 arylene, substituted or unsubstituted C5-C30 heteroarylene, substituted or unsubstituted C1-C8 alkylene, and substituted or unsubstituted C1-C8 alkyleneoxy; and Ar1 and Ar2 each independently have a structure shown in Chemical Formula 2:

Chemical Formula 2

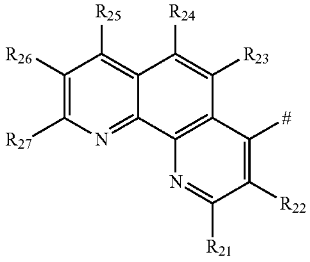

wherein $R_{21}$ to $R_{27}$ are each independently selected from hydrogen, substituted or unsubstituted C6-C18 aryl, substituted or unsubstituted pyridyl, substituted or unsubstituted quinolyl, substituted or unsubstituted C1-C16 alkyl, substituted or unsubstituted C1-C16 alkoxy, hydroxyl, and carboxyl; and # indicates a bonding position where the Chemical Formula 2 is bonded to the Chemical Formula 1.

In another aspect, the present disclosure provides a display panel including an organic electroluminescent device, wherein the organic electroluminescent device comprises a substrate, an anode, a cathode arranged opposite to the anode, a first capping layer located at a side of the cathode facing away from the anode, and organic functional layers located between the anode and the cathode, wherein the organic functional layers comprise an electron injection layer, an electron transmission layer, a light-emitting layer, a hole transmission layer, and a second capping layer, and at least one of the electron injection layer, the electron transmission layer, or the light-emitting layer contains the organic compound as described above.

In still another aspect, the present disclosure provides a display apparatus including the above-mentioned display panel.

BRIEF DESCRIPTION OF DRAWINGS

In order to more clearly illustrate technical solutions of embodiments of the present disclosure, the accompanying drawings used in the embodiments and in the related art are briefly described below. The drawings described below are merely a part of the embodiments of the present disclosure. Based on these drawings, those skilled in the art can obtain other drawings without any creative effort.

DESCRIPTION OF EMBODIMENTS

The present disclosure is further described by the following examples and comparative examples, which are merely intended to illustrate the invention, but not to limit the present disclosure. Modifications or equivalents to the technical solutions according to the present disclosure should fall within the scope according to the present disclosure.

The present disclosure provides an organic compound containing anthryl and phenanthrolinyl, a display panel and a display device.

Figure 1:
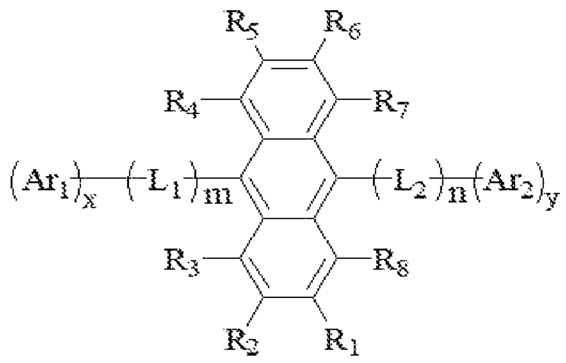
FIG. 1 is a Chemical Formula of an organic compound according to an embodiment of the present disclosure.

According to an aspect of the present disclosure, an organic compound containing anthryl and an phenanthrolinyl is provided and the organic compound has a structure represented by Chemical Formula 1 as shown in FIG. 1, Chemical Formula 1

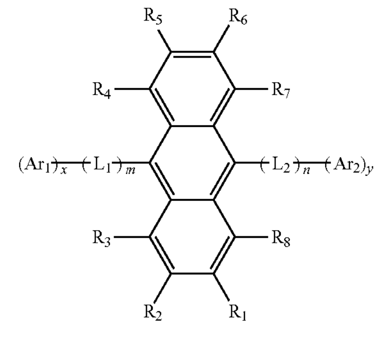

In this formula, $R_1$ to $R_8$ are each independently selected from hydrogen, substituted or unsubstituted C6-C18 aryl, substituted or unsubstituted pyridyl, substituted or unsubstituted quinolyl, substituted or unsubstituted C1-C16 alkyl, substituted or unsubstituted or substituted C1-C16 alkoxyl, hydroxyl, and carboxyl;

m, n, x and y each independently represent 0 or 1, where $m+x \geq 1$, $n+y \geq 1$, $m+n \geq 1$, and $x+y \geq 1$;

$L_1$ and $L_2$ are each independently selected from a substituted or unsubstituted C6-C30 arylene, substituted or unsubstituted C5-C30 heteroarylene, substituted or unsubstituted C1-C8 alkylene, and substituted or unsubstituted C1-C8 alkyleneoxy; and Ar1 and Ar2 each independently have a structure shown in Chemical Formula 2:

Chemical Formula 2

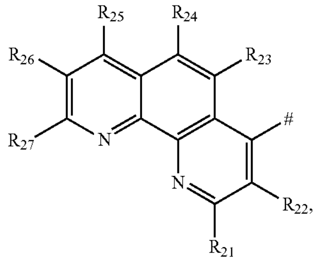

In this formula, $R_{21}$ to $R_{27}$ are each independently selected from hydrogen, substituted or unsubstituted C6-C18 aryl, substituted or unsubstituted pyridyl, substituted or unsubstituted quinolyl, substituted or unsubstituted C1-C16 alkyl, substituted or unsubstituted C1-C16 alkoxy, a hydroxyl, and carboxyl; and # indicates a bonding position where the Chemical Formula 2 is bonded to the Chemical Formula 1.

The organic compound according to the present disclosure contains anthryl and phenanthrolinyl. The anthryl group is a rigid planar structure, which is advantageous for increasing the glass transition temperature of the material. Moreover, the rigid structure of the anthryl group also greatly improves the thermal stability of the molecule. The phenanthrolinyl group is an excellent electron-deficient group, and is widely used as the chemical group in the electron transmission layer. The organic compound provided by the present disclosure contains both the anthryl group and the phenanthrolinyl group and has the advantages of both of the above two groups, and thus can be used as a blue luminescent material, an electron transmission material, or a material with both electron transmission and light emission functions.

According to an embodiment of the present disclosure, in the Chemical Formula 1, $L_1$ and $L_2$ each independently represent one of the following structures:

Chemical Formula 2-1

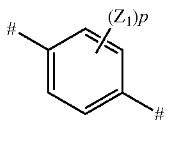

Chemical Formula 2-2

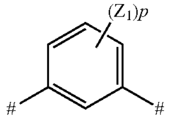

Chemical Formula 2-3

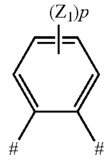

-continued

Chemical Formula 2-4

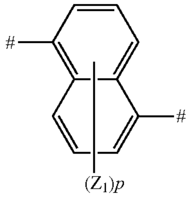

Chemical Formula 2-5

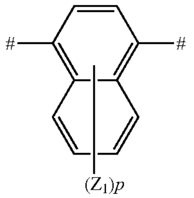

Chemical Formula 2-6

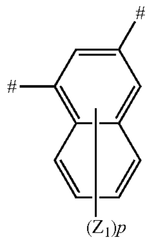

Chemical Formula 2-7

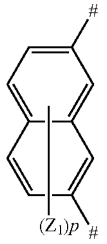

Chemical Formula 2-8

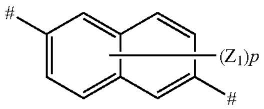

Chemical Formula 2-9

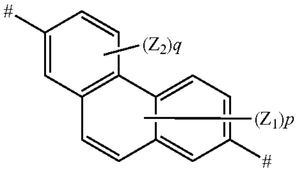

Chemical Formula 2-10

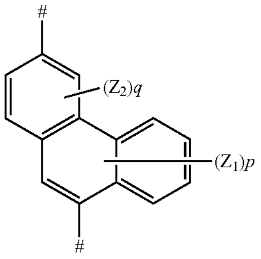

Chemical Formula 2-11

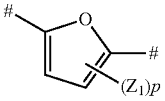

-continued

Chemical Formula 2-12

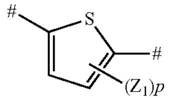

Chemical Formula 2-13

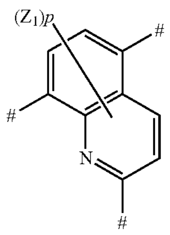

Chemical Formula 2-14

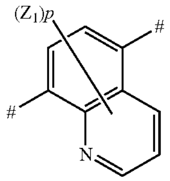

Chemical Formula 2-15

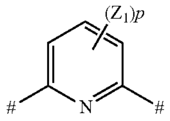

Chemical Formula 2-16

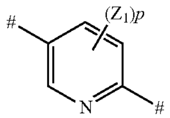

Chemical Formula 2-17

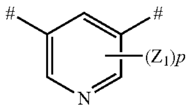

Chemical Formula 2-18

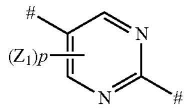

Chemical Formula 2-19

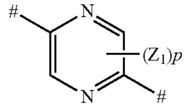

Chemical Formula 2-20

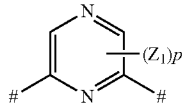

in which, $Z_1$ and $Z_2$ are each independently selected from hydrogen, substituted or unsubstituted C6-C30 aryl, substituted or unsubstituted C6-C30 fused aryl, substituted or unsubstituted C6-C30 fused heteroaryl, substituted or unsubstituted C1-C16 alkylene, and substituted or unsubstituted C1-C16 alkyleneoxy.

in Chemical Formulas 2-1 to 2-3, p represents any integer from 0 to 4;

in Chemical Formulas 2-4 to 2-8, p represents any integer from 0 to 6;

in Chemical Formulas 2 In 9 to 2-10, p represents any integer from 0 to 5, and q represents any integer from 0 to 3;

in Chemical Formulas 2-11, 2-12, 2-18, 2-19 and 2-20, p represents any integer from 0 to 2;

in the Chemical Formulas 2-15 to 2-17, p represents any integer from 0 to 3; and # indicates a bonding position where each of the Chemical Formulas 2-1 to 2-20 is bonded to the Chemical Formula 1.

According to an embodiment of the present disclosure, in the Chemical Formula 1, $L_1$ and $L_2$ each independently represent one of the following structures:

Chemical Formula 3-1

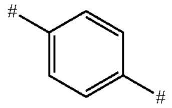

Chemical Formula 3-2

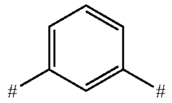

Chemical Formula 3-3

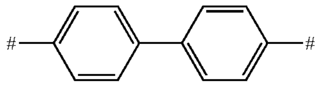

Chemical Formula 3-4

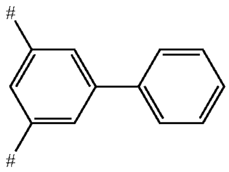

Chemical Formula 3-5

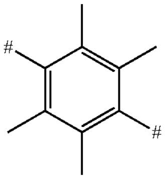

Chemical Formula 3-6

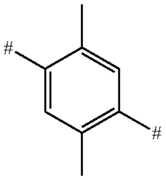

Chemical Formula 3-7

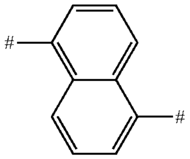

Chemical Formula 3-8

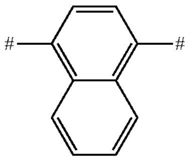

-continued

Chemical Formula 3-9

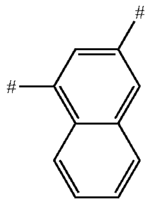

Chemical Formula 3-10

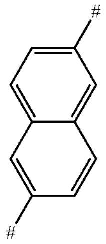

Chemical Formula 3-11

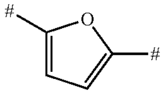

Chemical Formula 3-12

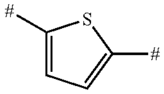

Chemical Formula 3-13

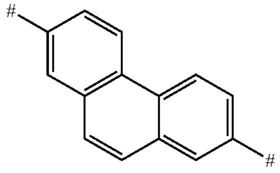

Chemical Formula 3-14

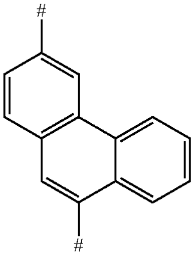

Chemical Formula 3-15

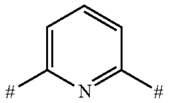

Chemical Formula 3-16

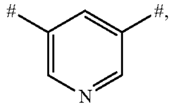

in which, # indicates a bonding position where each of the Chemical Formulas 3-1 to 3-16 is bonded to the Chemical Formula 1.

According to an embodiment of the present disclosure, in the Chemical Formula 1, m=0, n=1, x=1, and y=0.

According to an embodiment of the present disclosure, in the Chemical Formula 1, m=0, n=1, x=0, and y=1.

According to an embodiment of the present disclosure, in the Chemical Formula 1, m=0, n=1, and x=y=1.

According to an embodiment of the present disclosure, in the Chemical Formula 1, m=1, n=0, and x=y=1.

According to an embodiment of the present disclosure, in the Chemical Formula 1, m=n=1, and x+y=1.
According to an embodiment of the present disclosure, in the Chemical Formula 1, m=n=1, and x=y=1.
According to an embodiment of the disclosure, the organic compound is further selected from the following compounds:
ET01
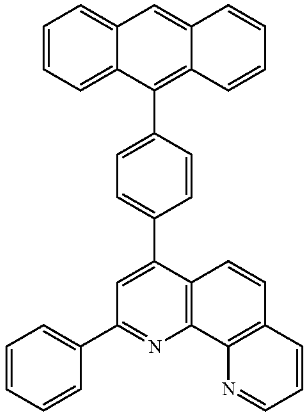
ET02
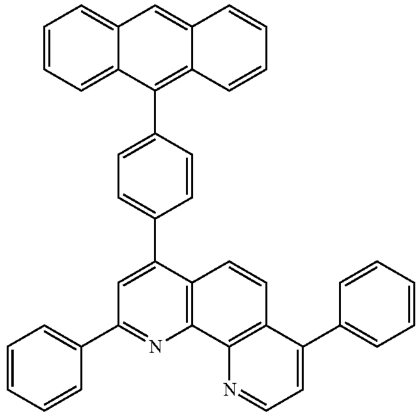
ET03
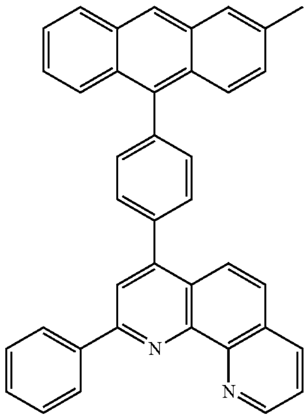
-continued
ET04
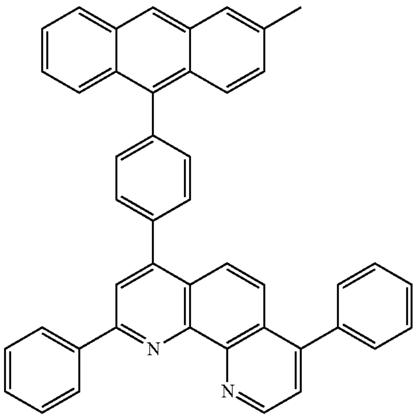
ET05
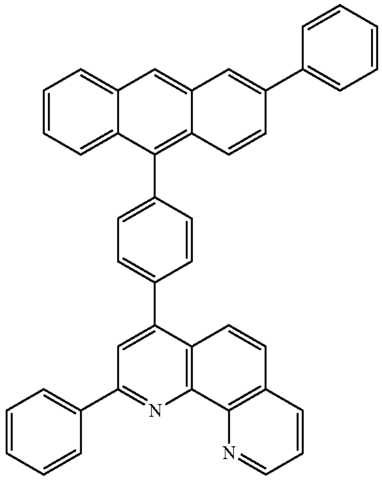
ET06
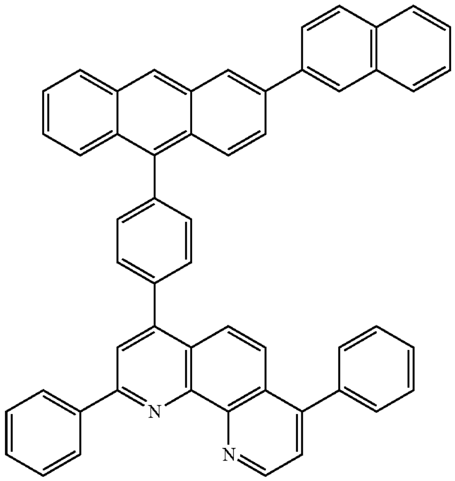

-continued
ET07
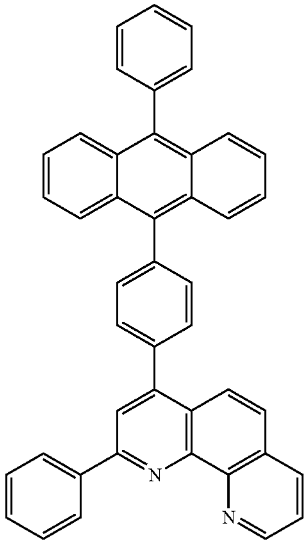
ET08
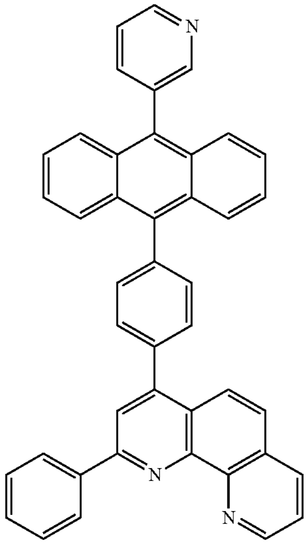
ET09
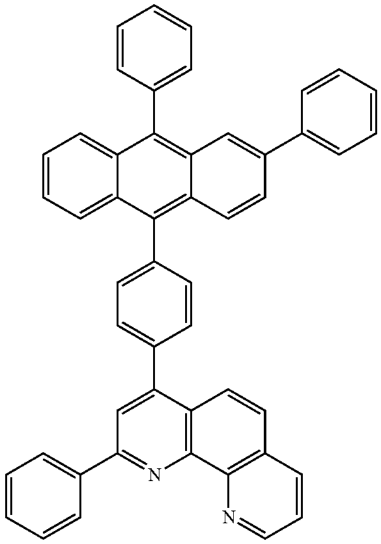
-continued
ET10
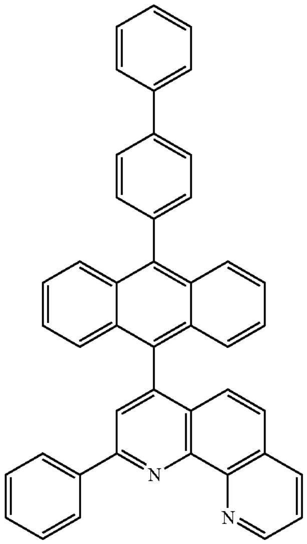
ET11
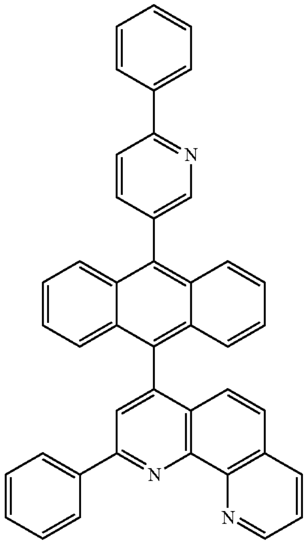
ET12
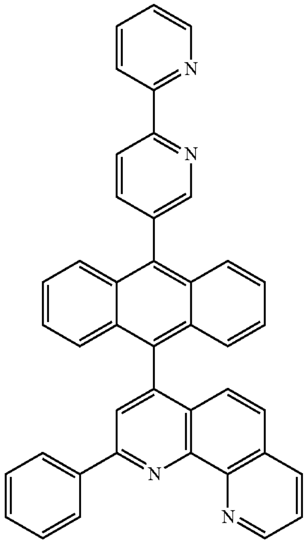

-continued
ET13
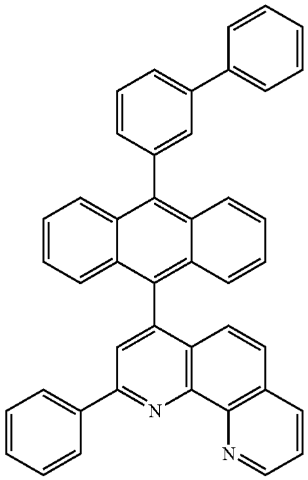
ET14
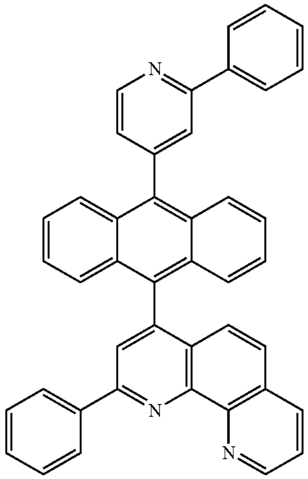
ET15
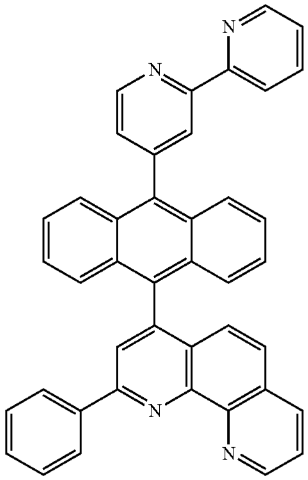
-continued
ET16
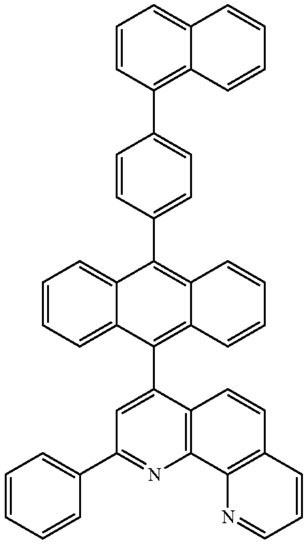
ET17
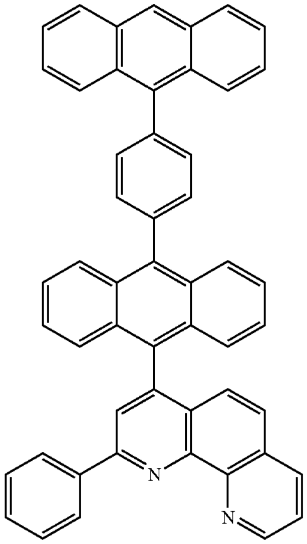
ET18
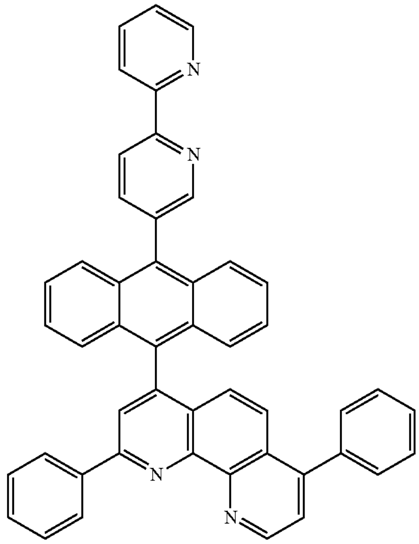

-continued
ET19
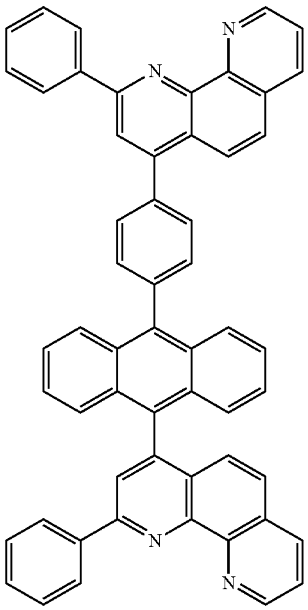
ET20
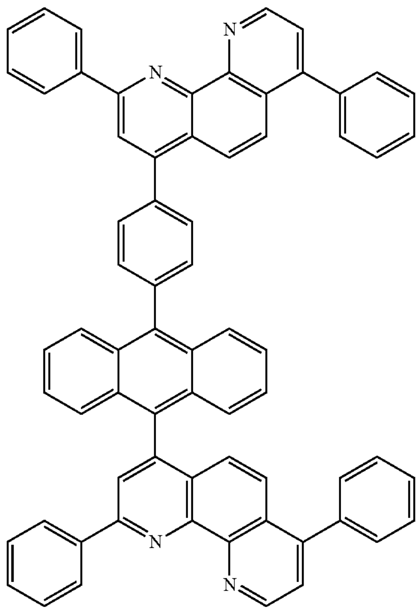
-continued
ET21
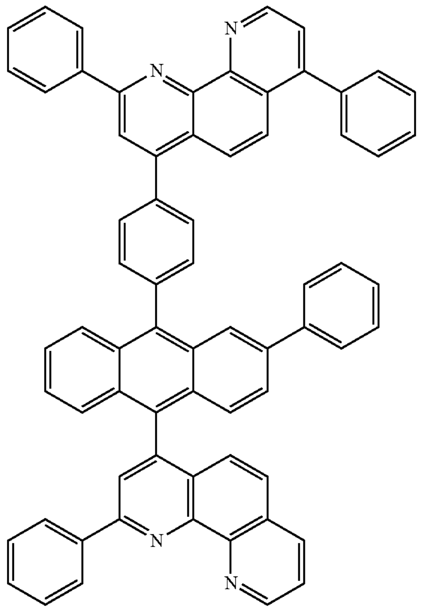
ET22
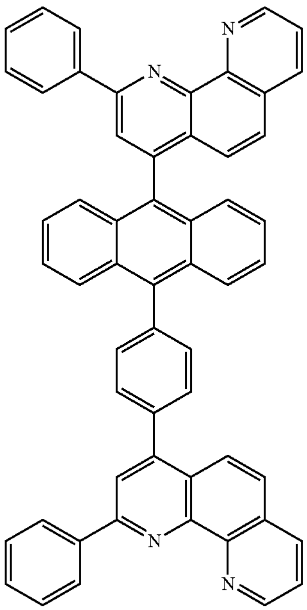

-continued
ET23
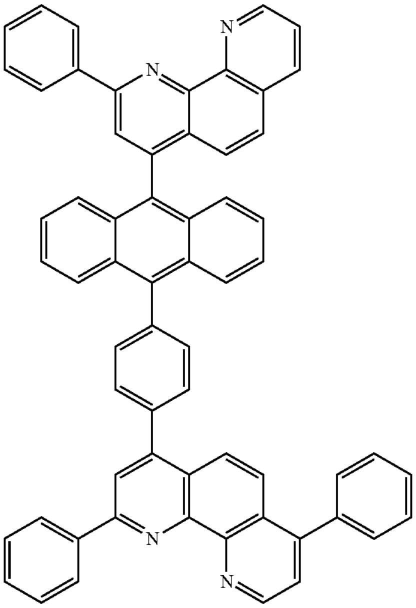
ET24
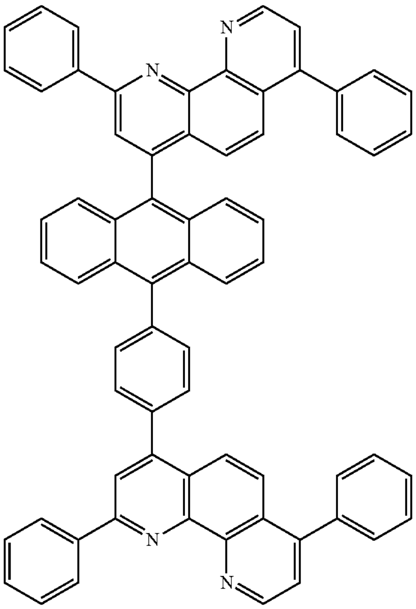
-continued
ET25
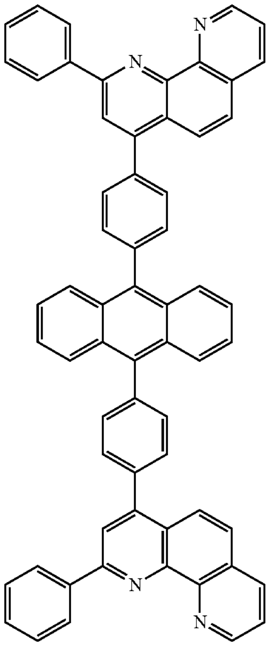
ET26
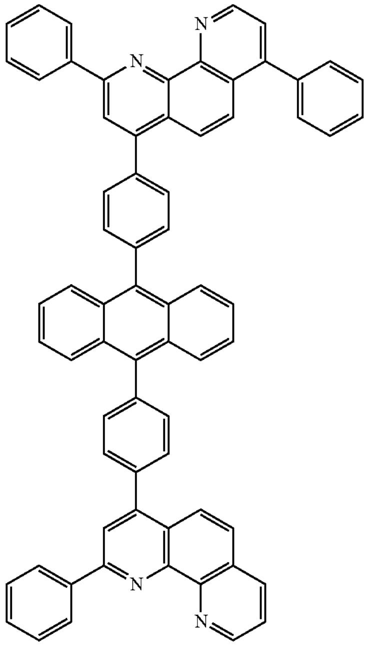

-continued
ET27
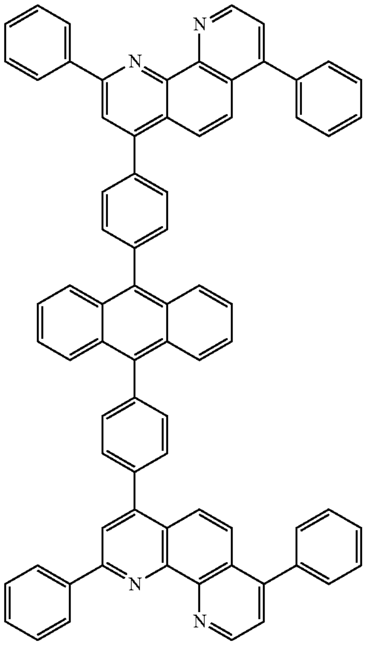
ET28
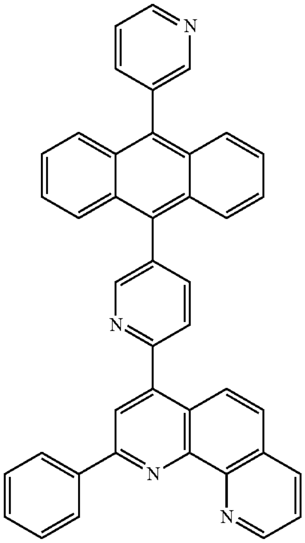
-continued
ET29
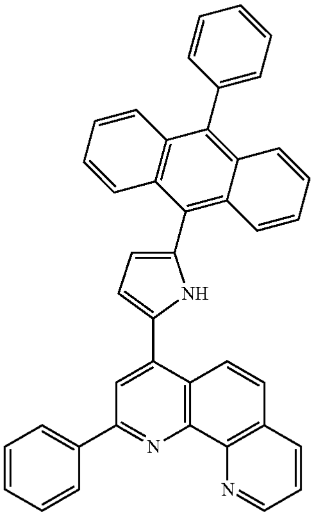
ET30
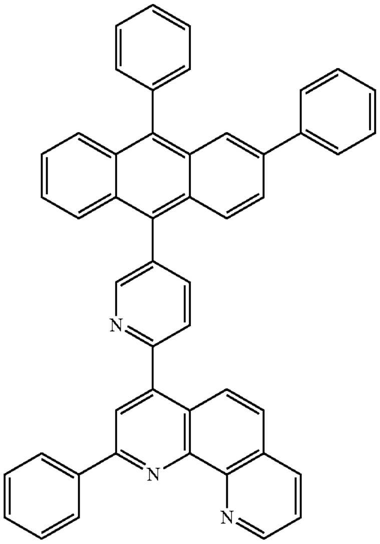
ET31
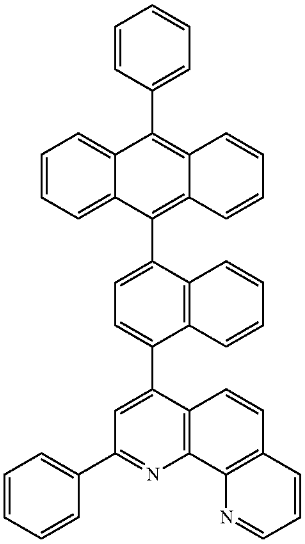

-continued

ET32

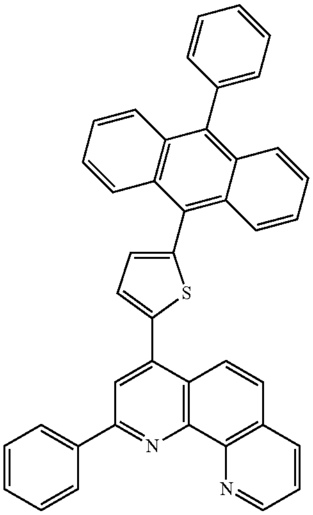

ET33

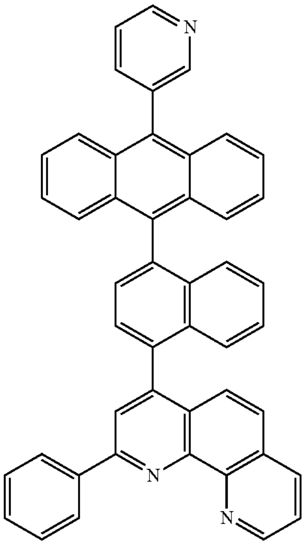

ET34

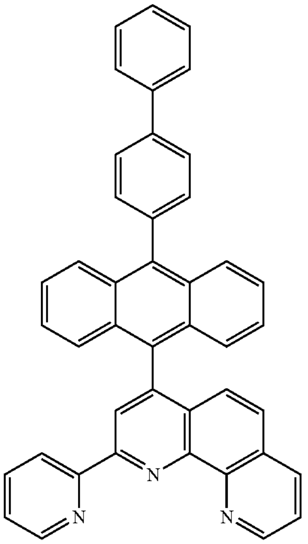

-continued

ET35

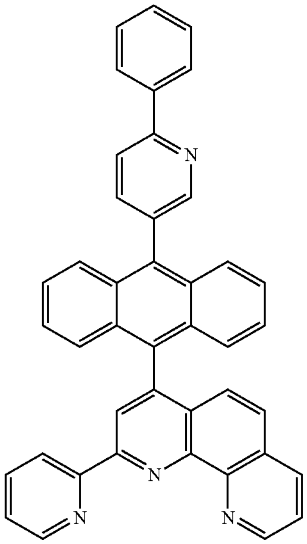

ET36

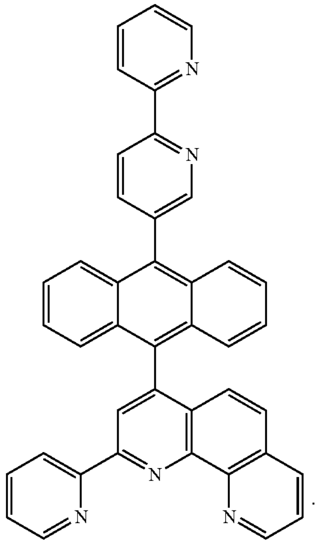

According to an embodiment of the present disclosure, the organic compound represented by the Chemical Formula 1 has a glass transition temperature greater than or equal to 120° C.

Another aspect of the present disclosure provides a display panel including an organic electroluminescent device. The organic electroluminescent device includes a substrate, an anode, a cathode arranged opposite to the anode, a first capping layer located at a side of the cathode facing away from the anode, and organic functional layers located between the anode and the cathode. The organic functional layers include an electron injection layer, an electron transmission layer, a light-emitting layer, a hole transmission layer, and a second capping layer. At least one of the electron injection layer, the electron transmission layer, or the light-emitting layer contains the organic compound containing anthryl and phenanthrolinyl as described above.

According to an embodiment of the display panel of the present disclosure, an energy difference between a LUMO energy level of a material of the electron transmission layer and a LUMO energy level of a material of the light-emitting layer or the electron injection layer is less than 0.2 eV; and an energy of a HOMO energy level of the material of the electron transmission layer is at least 0.3 eV greater than an energy of a HOMO level of the material of the electron injection layer.

According to an embodiment of the display panel of the present disclosure, the electron injection layer includes: the above-described organic compound containing anthryl and phenanthrolinyl, and a doping metal.

According to an embodiment of the display panel of the present disclosure, the doping metal is selected from a group consisting of sodium, potassium, calcium, cesium, ytterbium, and combinations thereof.

According to an embodiment of the display panel of the present disclosure, the doping metal is dopped in the electron injection layer in an amount of from 1% by weight to 5% by weight.

According to an embodiment of the display panel of the present disclosure, the doping metal is dopped in the electron injection layer in an amount of 3% by weight.

In the organic electroluminescent device provided by the present disclosure, the anode can be made of metal selected from a group consisting of copper, gold, silver, iron, chromium, nickel, manganese, palladium, platinum, etc., and alloys thereof. The anode also can be made of metal oxide, such as indium oxide, zinc oxide, indium tin oxide (ITO), indium zinc oxide (IZO), and the like. The anode also can be made of a conductive polymer, such as polyaniline, polypyrrole, poly(3-methylthiophene) and the like. In addition to the anode materials mentioned above, the anode material can also be selected from materials that are conducive to hole injection and combinations thereof, including the suitable anode materials known in the related art.

In the organic electroluminescent device provided by the present disclosure, the cathode can be made of metal, such as aluminum, magnesium, silver, indium, tin, titanium, etc., or alloys thereof. The cathode also can be made of multiple-layer metal material, such as LiF/Al, $LiO_2$/Al, $BaF_2$/Al, and the like. In addition to the cathode materials listed above, the cathode material can also be selected from materials that are conducive to electron injection and combinations thereof, including the suitable cathode materials known in the related art.

In some embodiments of the present disclosure, the organic electroluminescent device is manufactured by forming an anode on a transparent or opaque smooth substrate, forming an organic thin layer on the anode, forming a cathode on the organic thin layer, and finally forming a capping layer (CPL) on the cathode. The organic thin layer can be formed by a known film forming method such as evaporation, sputtering, spin coating, dipping, ion plating, and the like. The materials of the electron injection layer, the electron transmission layer, and the light-emitting layer may be the organic compound containing anthryl and phenanthrolinyl described in the present disclosure. The CPL can be prepared by an evaporation method or a solution method. The solution method includes an ink-jet printing method, spin coating, blade coating, screen printing, roll-to-roll printing, and the like.

The novel organic compound containing anthryl and phenanthrolinyl can be used as the materials of the electron injection layer, the electron transmission layer, and the light-emitting layer.

Another aspect of the present disclosure provides a display device including the display panel as described above.

Synthesis of the organic compounds ET01, ET08, ET12, ET20, ET25 and ET34 is exemplarily described below.

Synthesis of Intermediate 2-phenyl-1,10-phenanthroline-4-chloro

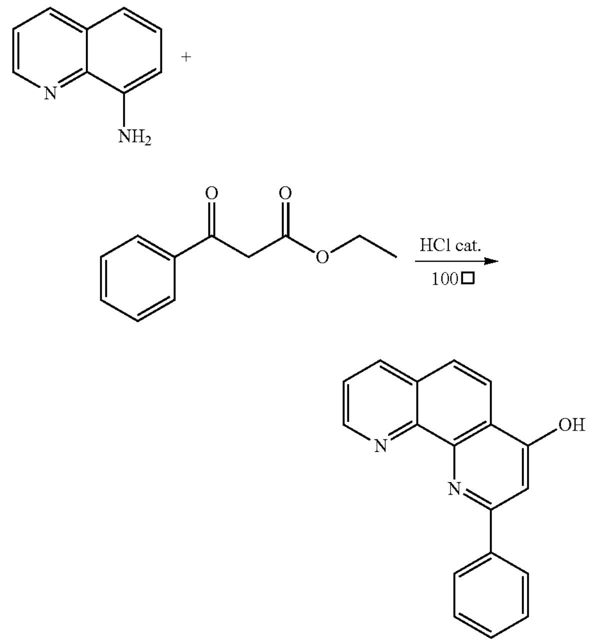

A mixture of 8-aminoquinoline (50 mmol) and ethyl acetoacetate (50 mmol) was stirred at 100° C. for 24 hours, and about 10 drops of HCl catalyst having a concentration of 10% was added to the mixture. The reaction mixture was cooled at room temperature, and then 20 mL toluene was added and then removed by rotary distillation under a reduced pressure. The same process as described above was repeated three times. The formed brown oily crude enamine was dissolved in 20 mL diphenyl ether, and 70 mL enamine solution was slowly added to diphenyl ether at 260° C. for 15 minutes. After 30 minutes, the reaction mixture was cooled to room temperature and then hexane was added to the reaction mixture. The mixture was then decanted to remove the solvent, and the residue was re-crystallised with dichloromethane and ethyl acetate to obtain a light brown solid 2-phenyl-1,10-phenanthroline-4-ol.

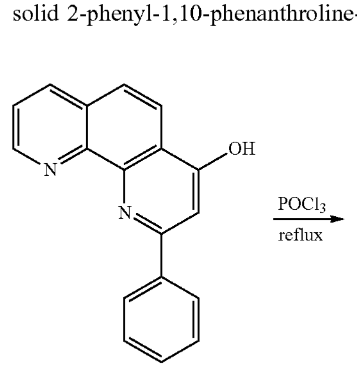

-continued

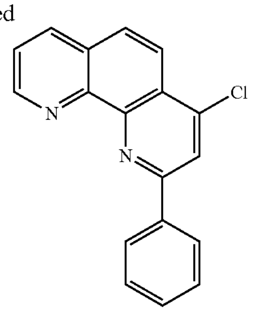

2-phenyl-1,10-phenanthroline-4-ol (25 mol) was slowly added to phosphorus oxychloride (60 mL) and then mixed for 4 hours. The reaction mixture was cooled to room temperature and the solvent in the reaction mixture was removed under a reduced pressure. The obtained solid was treated with dichloromethane and saturated $NaHCO_3$ to form an organic layer and an aqueous layer, and the organic layer was separated. The aqueous layer was further extracted with dichloromethane, and the further obtained organic layer was washed with brine, dried with $MgSO_4$, filtered and concentrated. The residue was recrystallized with dichloromethane and ethyl acetate to obtain a light brown solids of 2-phenyl-1,10-phenanthroline-4-chloro.

Example 1

Synthesis of Compound ET01

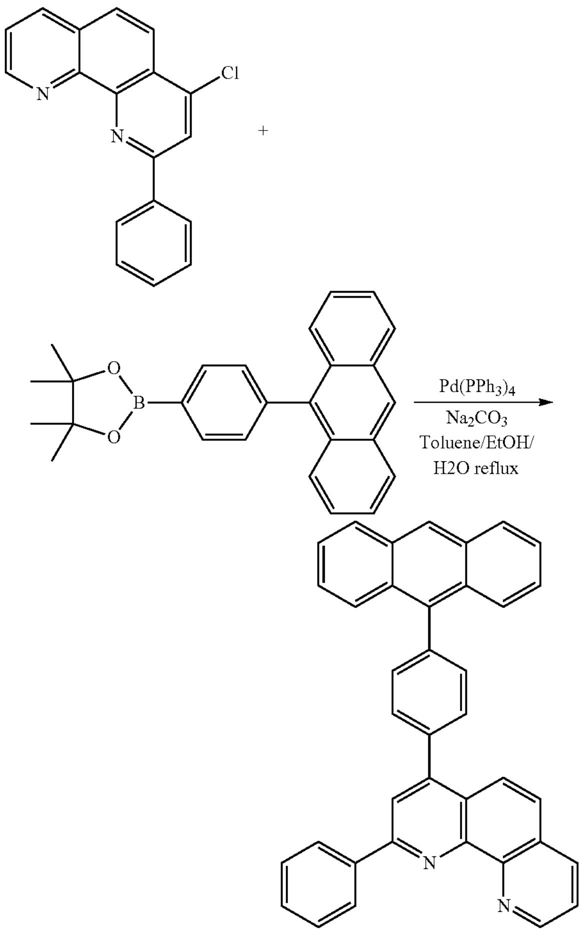

ET01

2-phenyl-1,10-phenanthroline-4-chloro (10 mmol), 4-(9-anthryl)phenylboronic acid pinacol ester (10 mmol) and $Na_2CO_3$ (80 mmol) were added to a solvent of toluene/EtOH (absolute ethanol)/$H_2O$ (75/25/50, mL) to form a mixed solution. Then, tetrakis(triphenylphosphine)palladium $Pd(PPh_3)_4$ (0.48 mmol) was added to the above mixed solution, and a reflux reaction was carried out for 20 hours under a nitrogen atmosphere. The obtained mixture was then cooled to room temperature and extracted with ethyl acetate. The aqueous layer was further extracted with dichloromethane and the further obtained organic layer was washed with brine, dried with $MgSO_4$, filtered and concentrated. The residue was recrystallized with dichloromethane and methanol to obtain a white solid compound ET01.

Elemental analysis of compound ET01 (Molecular Formula $C_{38}H_{24}N_2$): theoretical value: C, 89.74; H, 4.76; N, 5.51. Test value: C, 89.76; H, 4.75; N, 5.50. The ESI-MS (m/z) (M+) was obtained by liquid chromatography-mass spectrometry: theoretical value: 508.19, and test value: 508.36.

Example 2

Synthesis of Compound ET08

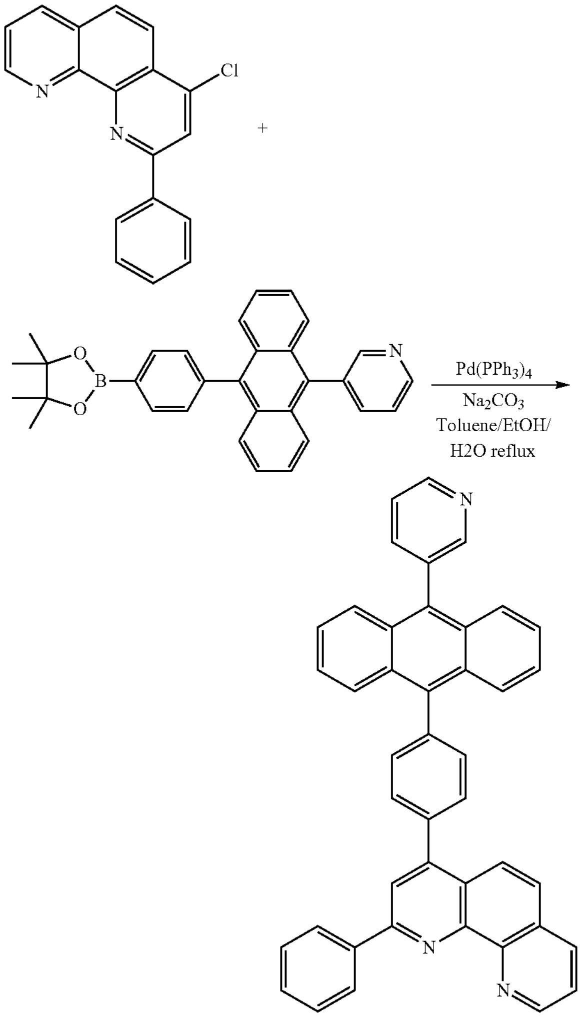

ET08

2-phenyl-1,10-phenanthroline-4-chloro (10 mmol), 4-(10-pyridyl-9-anthryl)phenyl boronic acid pinacol ester (10 mmol) and $Na_2CO_3$ (80 mmol) were added to a solvent of toluene/EtOH (absolute ethanol)/$H_2O$ (75/25/50, mL) to form a mixed solution. Then, $Pd(PPh_3)_4$ (0.48 mmol) was added to the above mixed solution, and a reflux reaction was carried out for 20 hours under a nitrogen atmosphere. The obtained mixture was then cooled to room temperature and extracted with ethyl acetate. The aqueous layer was further extracted with dichloromethane, and the further obtained organic layer was washed with brine, dried with $MgSO_4$, filtered and concentrated. The residue was recrystallized with dichloromethane and methanol to obtain a white solid compound ET08.

Elemental analysis of compound ET08 (Molecular Formula $C_{43}H_{27}N_3$): theoretical value: C, 88.18; H, 4.65; N, 7.17. Test value: C, 88.15; H, 4.66; N, 7.19. The ESI-MS (m/z) (M+) was obtained by liquid chromatography-mass spectrometry: theoretical value: 585.22, and test value: 585.51.

Example 3

Synthesis of Compound ET12

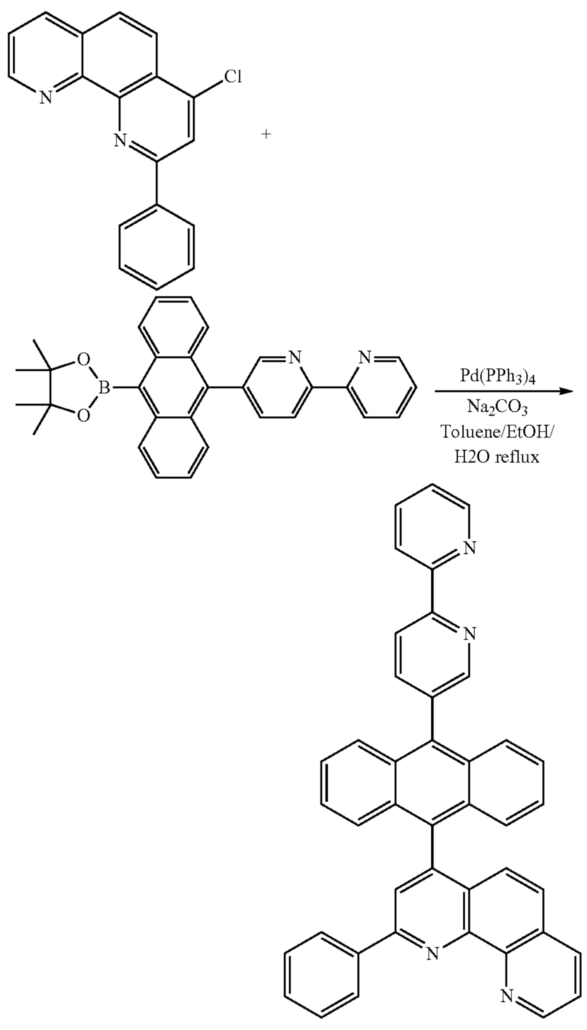

ET12

2-phenyl-1,10-phenanthroline-4-chloro (10 mmol), (10-bipyridyl-9-anthryl)boronic acid pinacol ester (10 mmol) and $Na_2CO_3$ (80 mmol) were added to a solvent of toluene/EtOH (absolute ethanol)/$H_2O$ (75/25/50, mL) to form a mixed solution. Then, $Pd(PPh_3)_4$ (0.48 mmol) was added to the above mixed solution, and a reflux reaction was carried out for 20 hours under a nitrogen atmosphere. The obtained mixture was then cooled to room temperature and extracted with ethyl acetate. The aqueous layer was further extracted with dichloromethane, and the further obtained organic layer was washed with brine, dried with $MgSO_4$, filtered and concentrated. The residue was recrystallized with dichloromethane and methanol to obtain a white solid compound ET12.

Elemental analysis of compound ET12 (Molecular Formula $C_{42}H_{26}N_4$): theoretical value: C, 85.98; H, 4.47; N, 9.55. Test value: C, 85.98; H, 4.48; N, 9.54. The ESI-MS (m/z) (M+) was obtained by liquid chromatography-mass spectrometry: theoretical value: 586.22, and test value: 586.43.

Example 4

Synthesis of Compound ET20

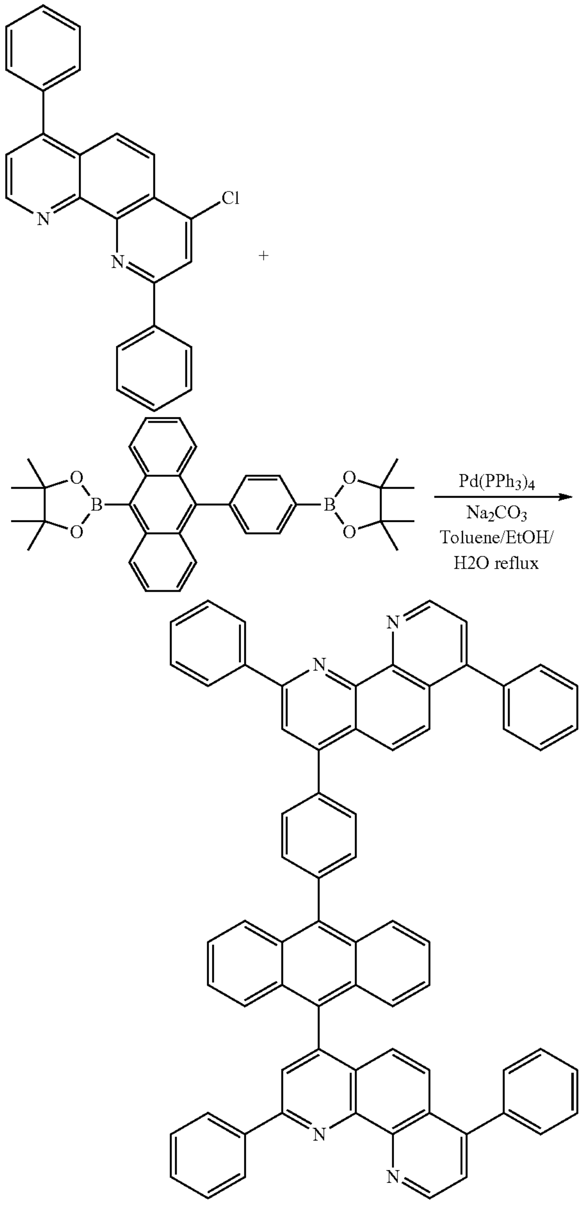

ET20

2,7-phenyl-1,10-phenanthroline-4-chloro (20 mmol), 4-boronic acid phenyl-9-(10-(4-phenylboronic acid pinacol ester)-9-anthryl)boronic acid pinacol ester (10 mmol) and $Na_2CO_3$ (80 mmol) were added to a solvent of toluene/EtOH (absolute ethanol)/$H_2O$ (75/25/50, mL) to form a mixed solution. Then, $Pd(PPh_3)_4$ (0.48 mmol) was added to the above mixed solution, and a reflux reaction was carried out for 20 hours under a nitrogen atmosphere. The obtained mixture was then cooled to room temperature and extracted with ethyl acetate. The aqueous layer was further extracted with dichloromethane, and the further obtained organic layer was washed with brine, dried with $MgSO_4$, filtered and concentrated. The residue was recrystallized with dichloromethane and methanol to obtain a white solid compound ET20.

Elemental analysis of compound ET20 (Molecular Formula $C_{68}H_{42}N_4$): theoretical value: C, 89.25; H, 4.63; N, 6.12. Test value: C, 89.26; H, 4.64; N, 6.10. The ESI-MS (m/z) (M+) was obtained by liquid chromatography-mass spectrometry: theoretical value: 914.34, and test value: 914.60.

Example 5

Synthesis of Compound ET25

2-phenyl-1,10-phenanthroline-4-chloro (20 mmol), (9,10-anthryl)bis (4-phenylboronic acid pinacol ester) (10 mmol) and $Na_2CO_3$ (80 mmol) were added to 啊 solvent of toluene/EtOH (absolute ethanol)/$H_2O$ (75/25/50, mL) to form a mixed solution. Then, $Pd(PPh_3)_4$ (0.48 mmol) was added to the above mixed solution, and a reflux reaction was carried out for 20 hours under a nitrogen atmosphere. The obtained mixture was then cooled to room temperature and extracted with ethyl acetate. The aqueous layer was further extracted with dichloromethane, and the further obtained organic layer was washed with brine, dried with $MgSO_4$, filtered and concentrated. The residue was recrystallized with dichloromethane and methanol to obtain a white solid compound ET25.

Elemental analysis of compound ET25 (Molecular Formula $C_{62}H_{38}N_4$): theoretical value: C, 88.76; H, 4.57; N, 6.68. Test value: C, 88.76; H, 4.58; N, 6.67. The ESI-MS (m/z) (M+) was obtained by liquid chromatography-mass spectrometry: theoretical value: 838.31, and test value: 838.43.

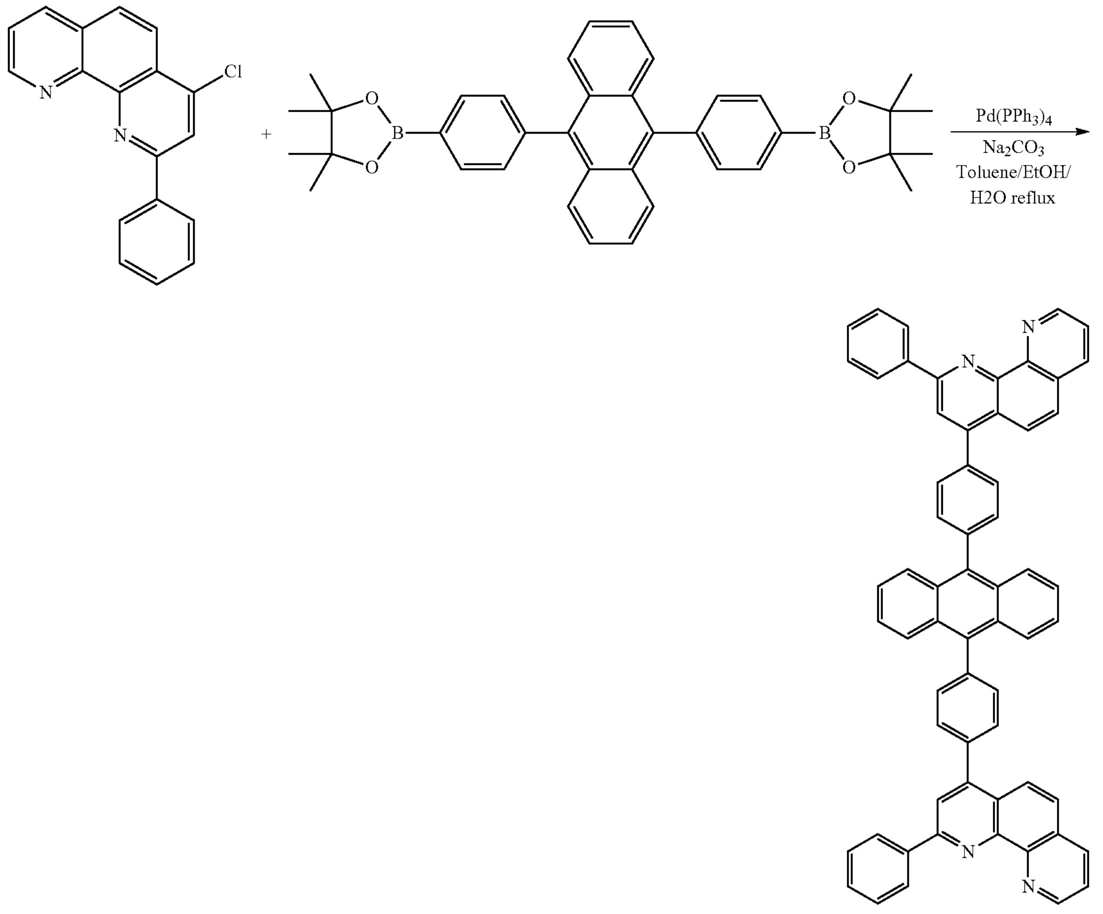

ET25

Example 6

Synthesis of Compound ET34

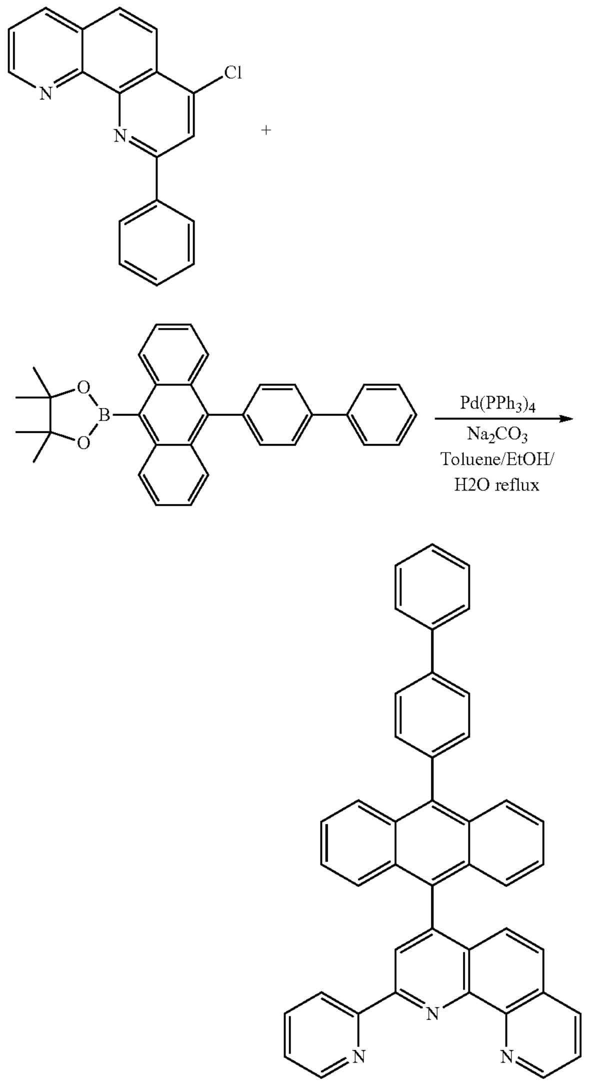

ET34

2-pyridyl-1,10-phenanthroline-4-chloro (10 mmol), (10-bipyridyl-9-anthryl) boronic acid pinacol ester (10 mmol) and $Na_2CO_3$ (80 mmol) were added to a solvent of toluene/EtOH (absolute ethanol)/$H_2O$ (75/25/50, mL) to form a mixed solution. Then, $Pd(PPh_3)_4$ (0.48 mmol) was added to the above mixed solution, and a reflux reaction was carried out for 20 hours under a nitrogen atmosphere. The obtained mixture was then cooled to room temperature and extracted with ethyl acetate. The aqueous layer was further extracted with dichloromethane, and the further obtained organic layer was washed with brine, dried with $MgSO_4$, filtered and concentrated. The residue was recrystallized with dichloromethane and methanol to obtain a white solid compound ET34.

Elemental analysis of compound ET34 (Molecular Formula $C_{43}H_{27}N_3$): theoretical value: C, 88.18; H, 4.65; N, 7.17. Test value: C, 88.18; H, 4.66; N, 7.16. The ESI-MS (m/z) (M+) was obtained by liquid chromatography-mass spectrometry: theoretical value: 585.22, and test value: 585.30.

Device Example 1

Figure 2:
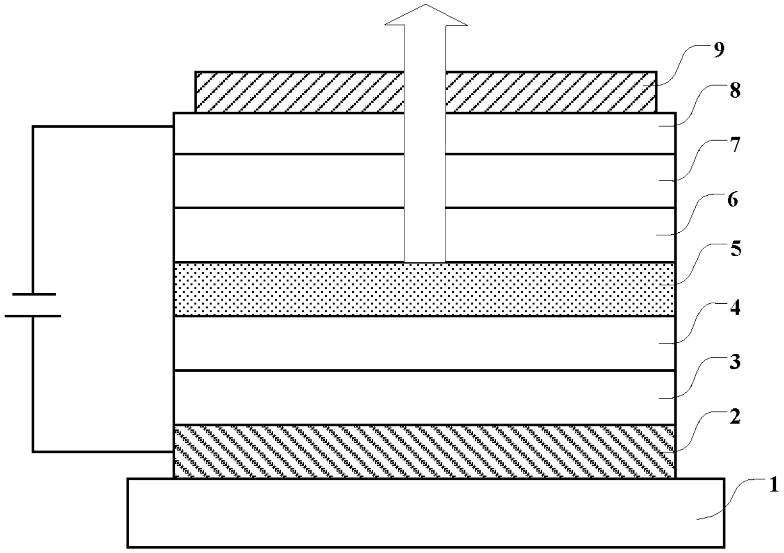
FIG. 2 is a structural schematic diagram showing an organic light-emitting device according to an embodiment of the present disclosure.

This example provides an organic electroluminscent device. As shown in FIG. 2, the organic electroluminscent device includes: a glass substrate 1, an ITO anode 2, a first hole transmission layer 3, a second hole transmission layer 4, a light-emitting layer 5, a first electron transmission layer 6, a second electron transmission layer 7, a cathode 8 (magnesium-silver electrode, a mass ratio of magnesium to silver is 9:1) and a capping layer (CPL) 9. The thickness of the ITO anode 2 is 15 nm. The thickness of the first hole transmission layer 3 is 10 nm. The thickness of the second hole transmission layer 4 is 95 nm. The thickness of the light-emitting layer 5 is 30 nm. The thickness of the first electron transmission layer 6 is 35 nm. The thickness of the second electron transmission layer 7 is 5 nm. The thickness of the magnesium-silver electrode 8 is 15 nm. The thickness of the capping layer (CPL) 9 is 100 nm.

The organic electroluminscent device of the present disclosure was prepared by the following steps:

1) The glass substrate 1 was cut into a size of 50 mm×50 mm×0.7 mm, respectively subjected to ultrasonic treatment in isopropyl alcohol and deionized water for 30 minutes, and then exposed to ozone for cleaning for about 10 minutes; the obtained glass substrate 1 with the ITO anode 2 was mounted to a vacuum deposition apparatus.

2) On the ITO anode 2, the hole injection layer material HAT-CN was vacuum evaporated to obtain a layer having a thickness of 10 nm as the first hole transmission layer 3.

3) Material TAPC was vacuum evaporated on the first hole transmission layer 3 to obtain a layer having a thickness of 95 nm as the second hole transmission layer 4.

4) DPVBi used as a host material and BCzVBi used as a doping material (a mass ratio of DPVBi to BCzVBi is 1:19) were co-deposited on the hole transmission layer 4 to form the light-emitting layer 5, and the thickness of the light-emitting layer 5 is 30 nm.

5) Material ET01 was vacuum evaporated on the light-emitting layer 5 to obtain the first electron transmission layer 6 having a thickness of 35 nm.

6) Material Alq3 was vacuum evaporated on the first electron transmission layer 6 to obtain the second electron transmission layer 7 having a thickness of 5 nm.

7) Magnesium and silver (the mass ratio of Mg to Ag is 9:1) were vacuum evaporated on the second electron transmission layer 7 to obtain the cathode 8 having a thickness of 15 nm.

8) A hole-type material CBP having a high refractive index was vacuum evaporated on the cathode 8 to obtain a cathode coating layer (capping layer or CPL) having a thickness of 100 nm.

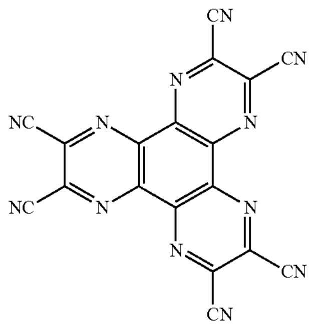
HAT-CN
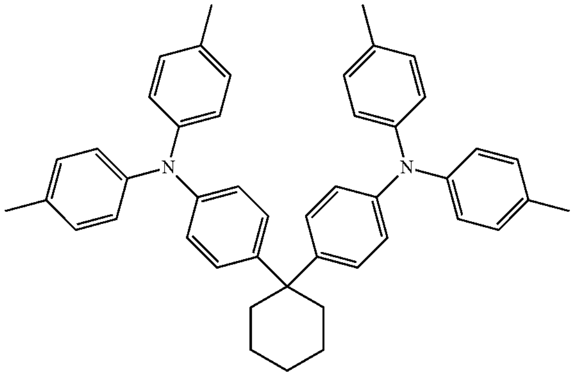
TAPC
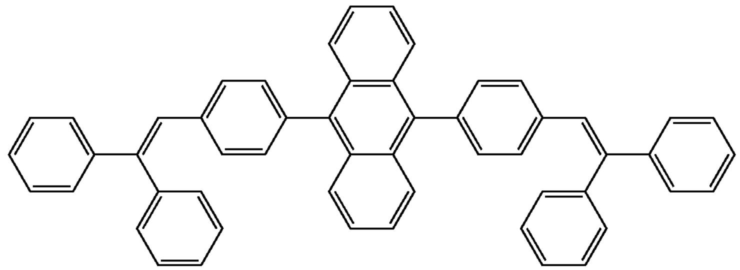
DPVBi
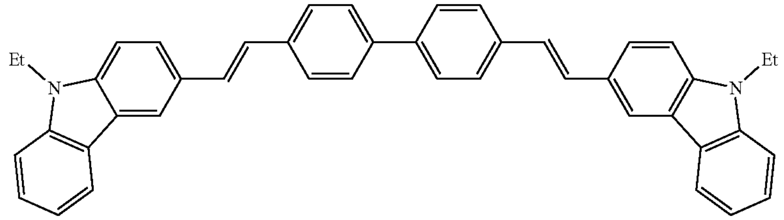
BCzVBi
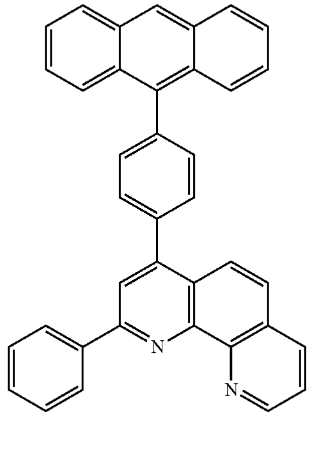
ET01
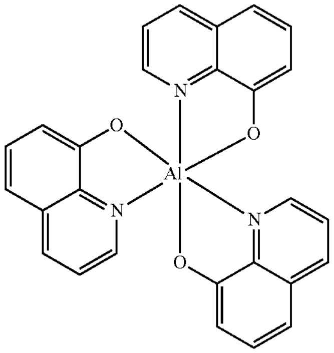
Alq3
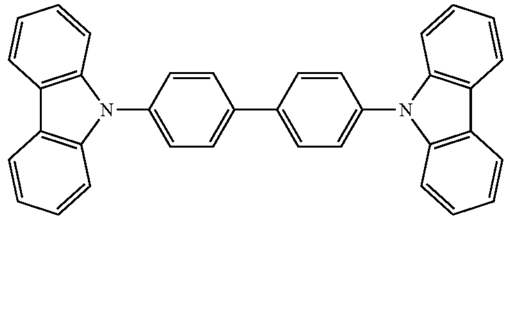
CBP Device Example 2

Compared with the Device Example 1, the device of the Device Example 2 was prepared by the same steps as in the Device Example 1 except that the first electron transmission layer 6 is made of ET08, while other layers were identical to those in the Device Example 1.

ET08

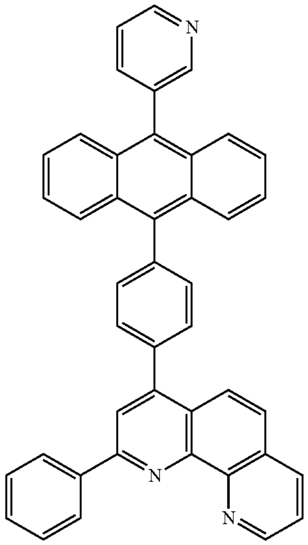

Device Example 3

Compared with the Device Example 1, the device of the Device Example 3 was prepared by the same steps as in the Device Example 1 except that the first electron transmission layer 6 is made of ET12, while other layers were identical to those in the Device Example 1.

ET12

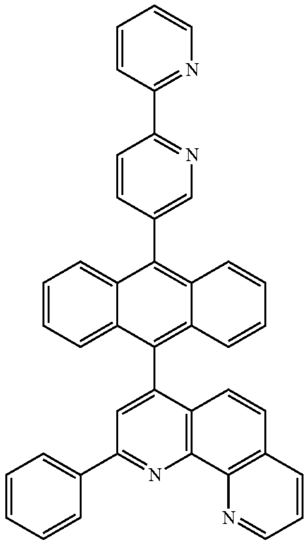

Device Example 4

Compared with the Device Example 1, the device of the Device Example 4 was prepared by the same steps as in the Device Example 1 except that the first electron transmission layer 6 is made of ET20, while other layers were identical to those in the Device Example 1.

ET20

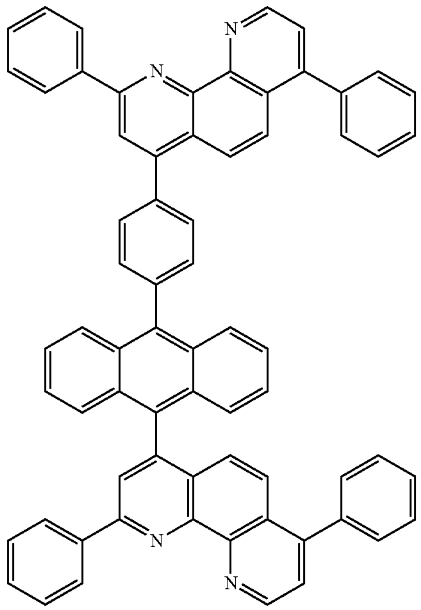

Device Example 5

Compared with the Device Example 1, the device of the Device Example 5 was prepared by the same steps as in the Device Example 1 except that the first electron transmission layer 6 is made of ET25, while other layers were identical to those in the Device Example 1.

ET25

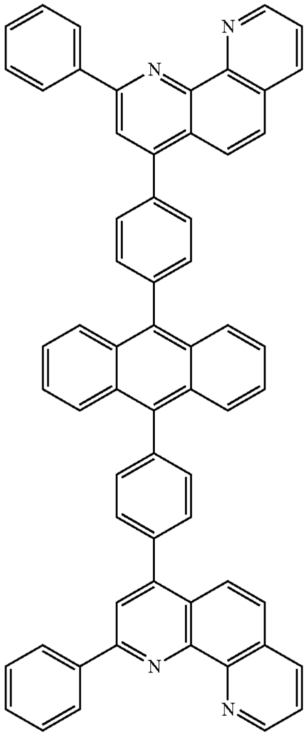

Device Example 6

Compared with the Device Example 1, the device of the Device Example 6 was prepared by the same steps as in the Device Example 1 except that the first electron transmission layer 6 is made of ET34, while other layers were identical to those in the Device Example 1.

ET34

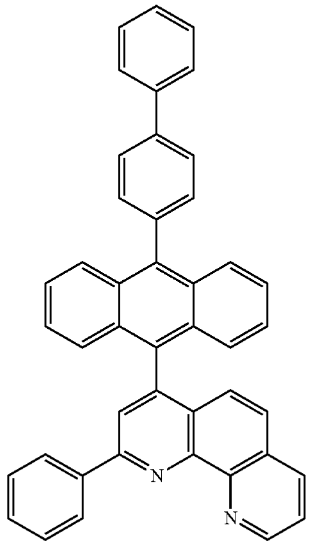

Device Comparative Example 1

Compared with the Device Example 1, the device of the Device Comparative Example 1 was prepared by the same steps as in the Device Example 1 except that the first electron transmission layer 6 is made of BPhen, while other layers were identical to those in the Device Example 1.

BPhen

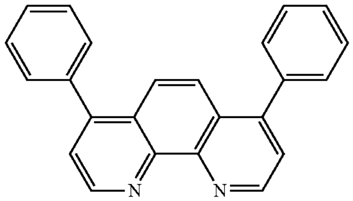

TABLE 1

Test Results for Device Examples and Device Comparative Example

| No. | Electron transmission material | Driving voltage (V) | Efficiency EQE/% | E/CIEy |
|---|---|---|---|---|
| Device Example 1 | ET01 | 3.80 | 5.89% | 76.1 |
| Device Example 2 | ET08 | 3.79 | 5.65% | 75.4 |
| Device Example 3 | ET12 | 3.85 | 5.23% | 70.8 |
| Device Example 4 | ET20 | 3.81 | 5.62% | 79.7 |
| Device Example 5 | ET25 | 3.78 | 5.14% | 76.9 |
| Device Example 6 | ET34 | 3.82 | 5.33% | 75.5 |
| Device Comparative Example 1 | BPhen | 4.08 | 4.13% | 62.4 |

As can be seen from the above Table 1, the optical devices using the organic compounds containing anthryl and phenanthrolinyl according to the present disclosure have a lower driving voltage, a higher current efficiency, a higher brightness, and a longer life time compared with the device comparative example 1.

Embodiments of the present disclosure further provide a display panel including the organic electroluminescent device as described above.

Embodiments of the present disclosure further provide an organic light-emitting display apparatus comprising the above-mentioned display panel.

Figure 3:
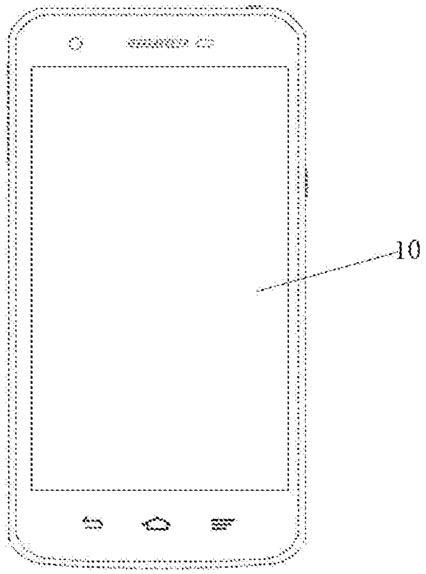
FIG. 3 is a schematic diagram showing a display apparatus according to an embodiment of the present disclosure.

In the present disclosure, the organic electroluminescent device may be an OLED, which may be used in an organic light-emitting display apparatus. The organic light-emitting display apparatus may be a mobile phone display screen, a computer display screen, a liquid crystal television display screen, a smart watch display screen, or a smart car display panel, VR or AR helmet display screen, and display screens of various smart devices, etc. FIG. 3 is a schematic diagram showing a display apparatus according to an embodiment of the present disclosure, in which the reference number 10 denotes a mobile phone display screen.

The above embodiments of the present disclosure are several preferred embodiments, but not intended to limit the scope of the claims. Any change and modification can be made by those skilled in the art without departing from the scope of the present application. The scope of protection is defined by the claims.

What is claimed is:

1. An organic compound being selected from the following compounds:

ET01

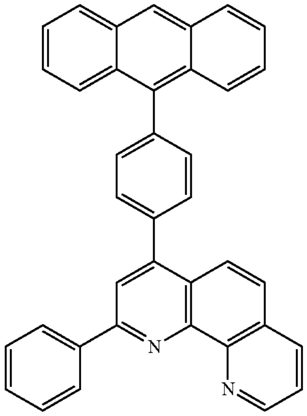

ET02

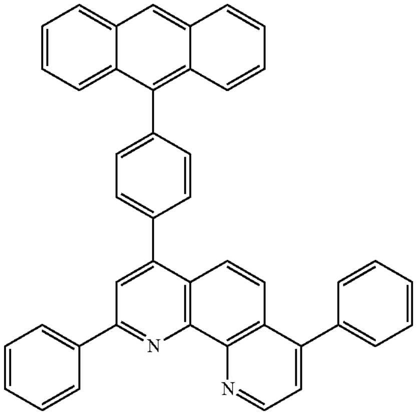

-continued
ET03
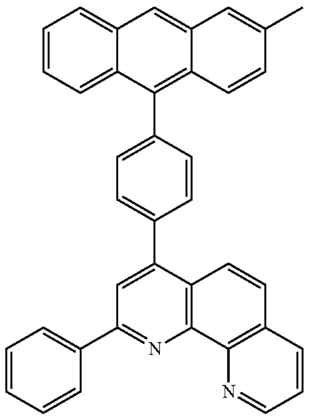
ET04
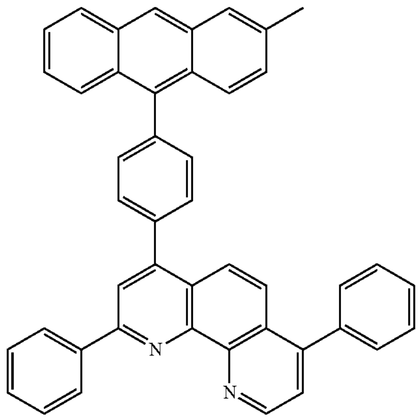
ET05
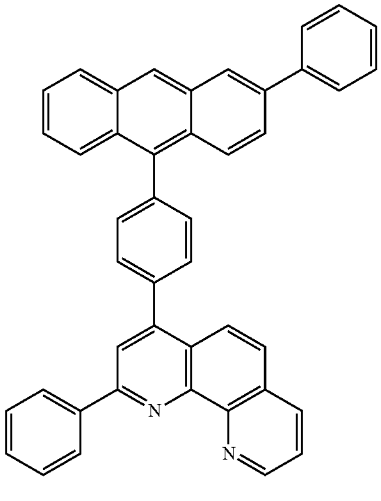
-continued
ET06
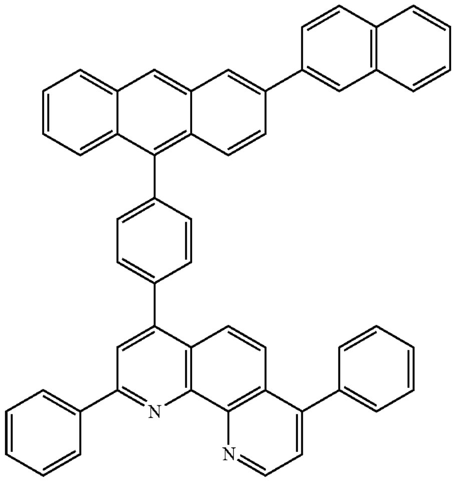
ET07
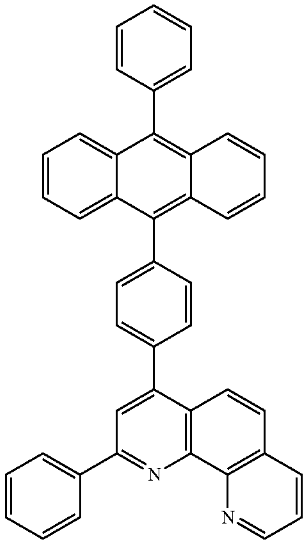
ET08
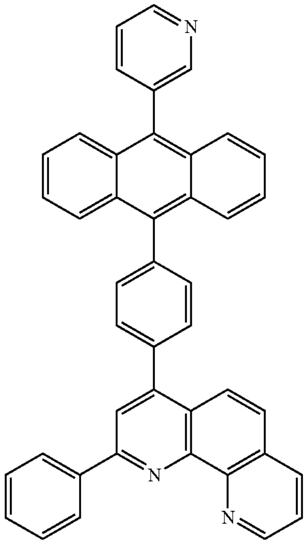

-continued
ET09
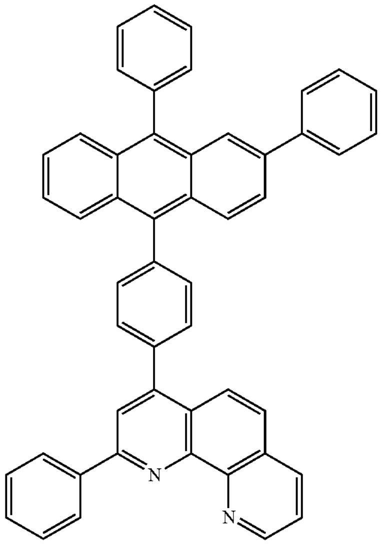
ET10
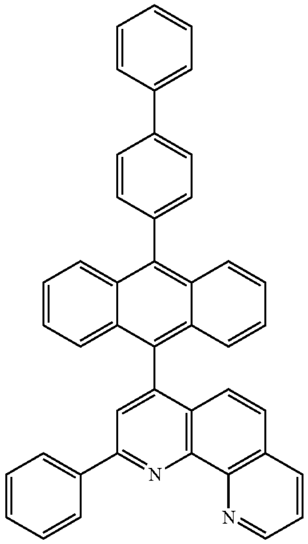
ET11
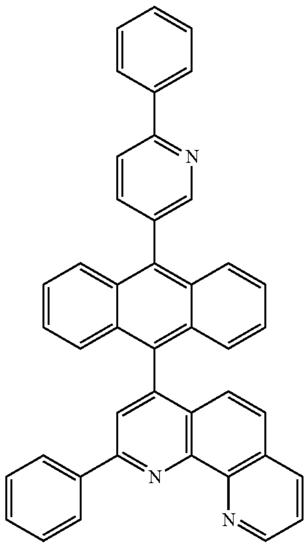
-continued
ET12
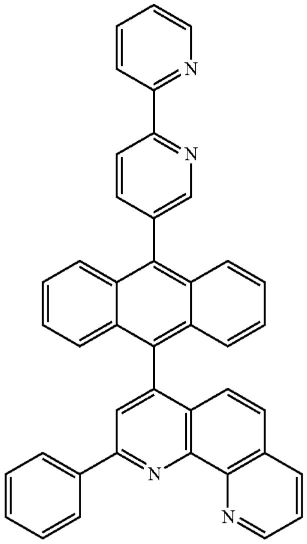
ET13
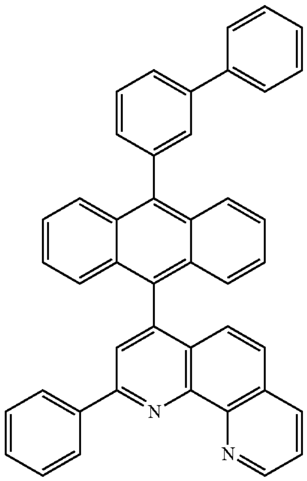
ET14
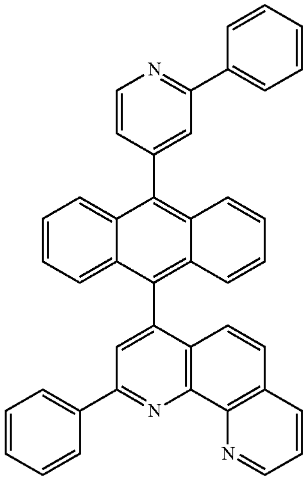

-continued
ET15
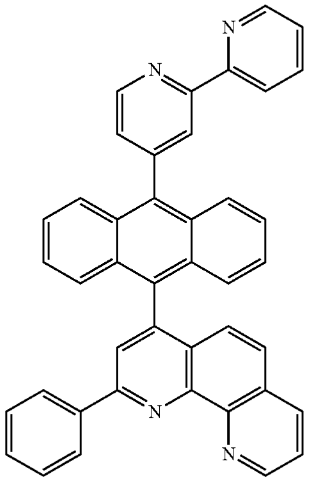
ET16
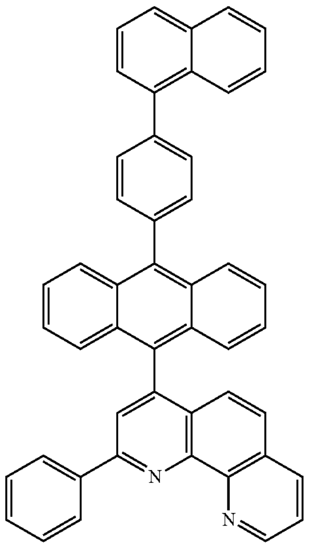
ET17
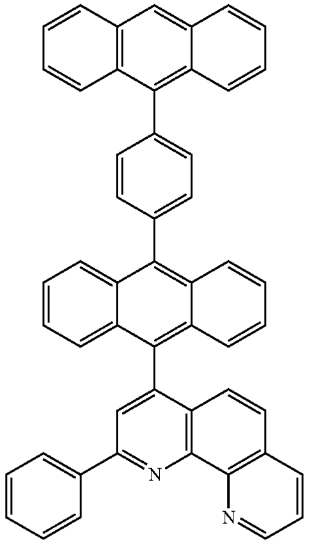
-continued
ET18
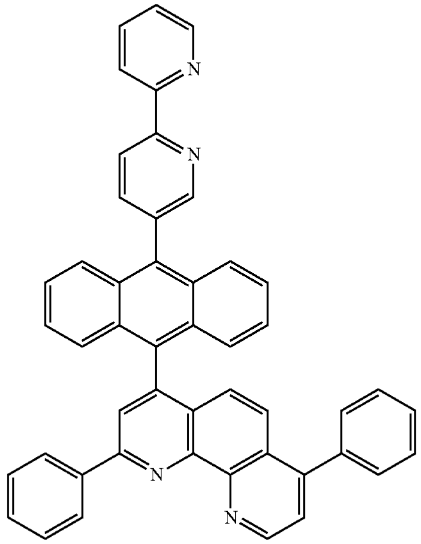
ET19
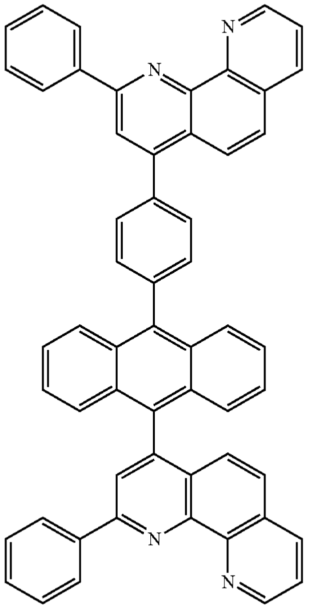

-continued
ET20
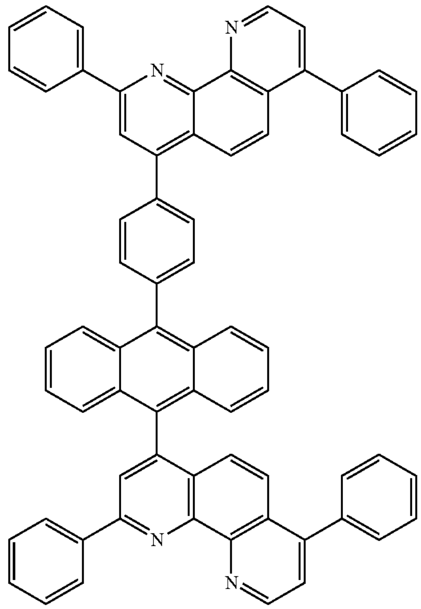
ET21
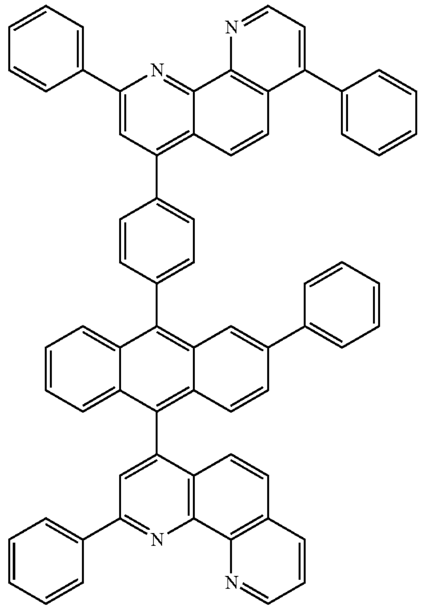
-continued
ET22
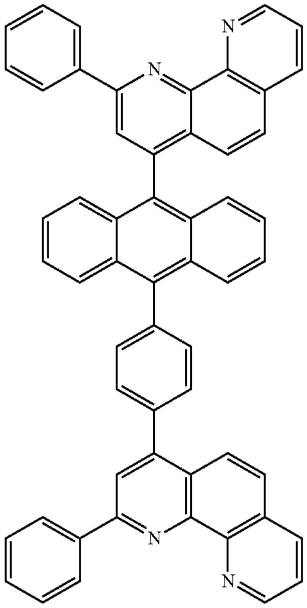
ET23
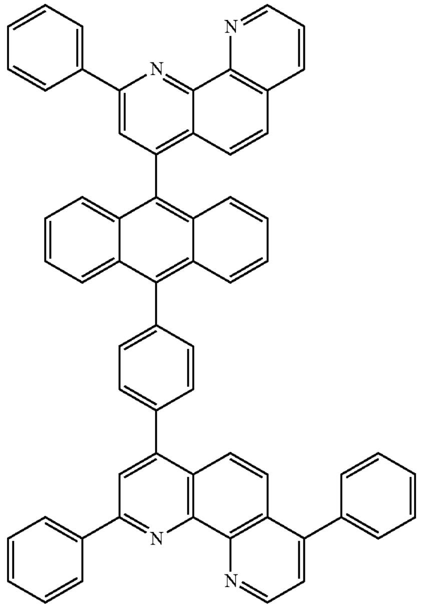

-continued
ET24
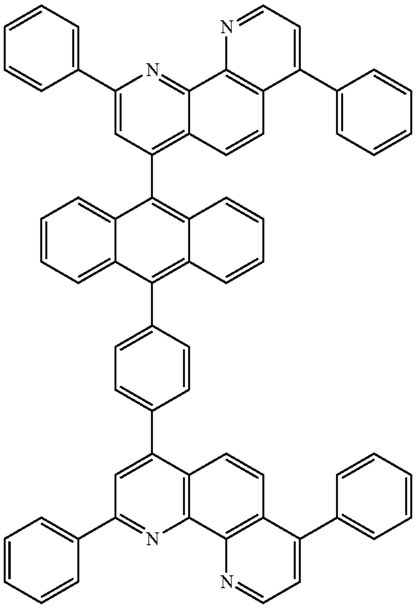
ET25
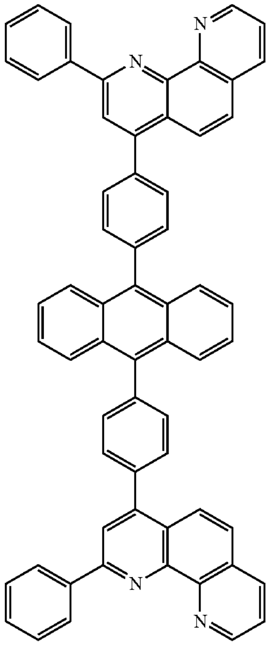
-continued
ET26
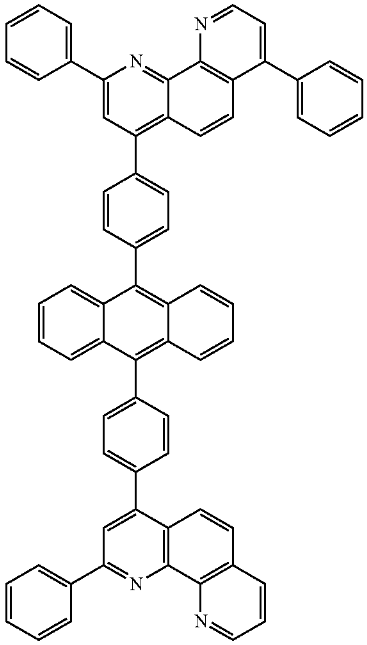
ET27
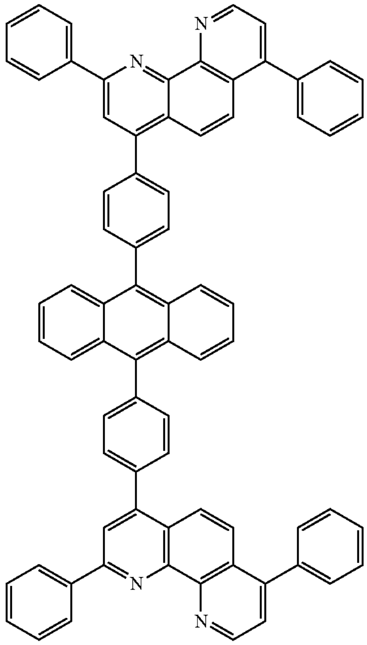

-continued
ET28
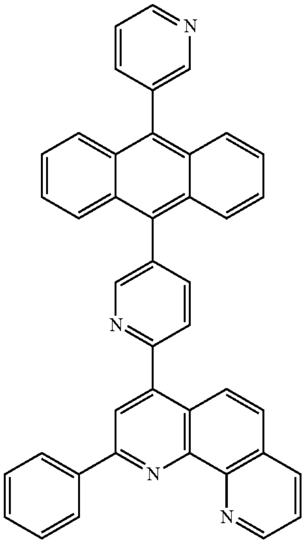
ET29
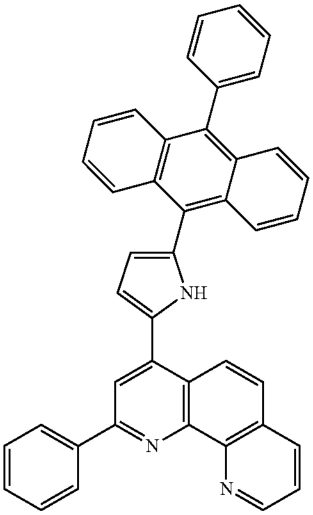
ET30
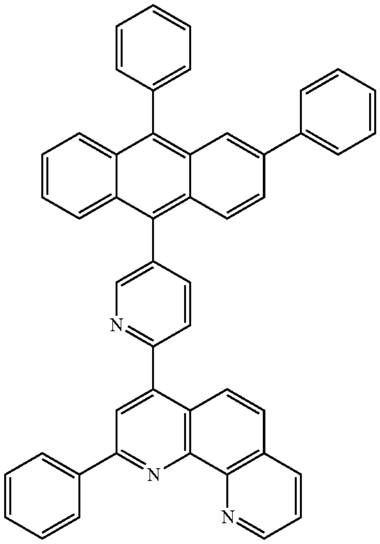
-continued
ET31
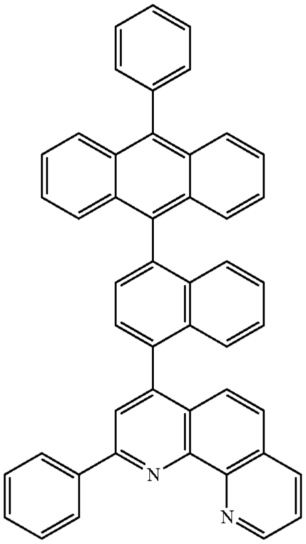
ET32
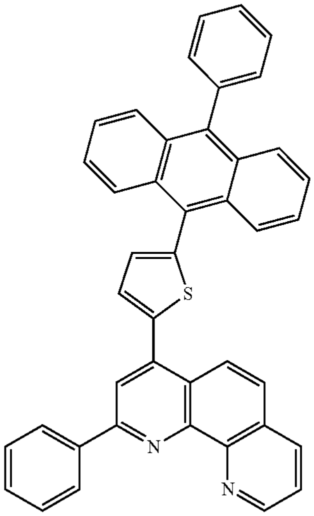
ET33
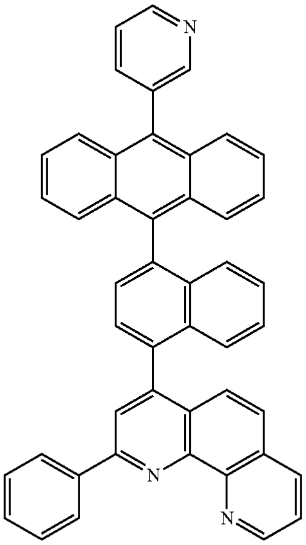

-continued

ET34

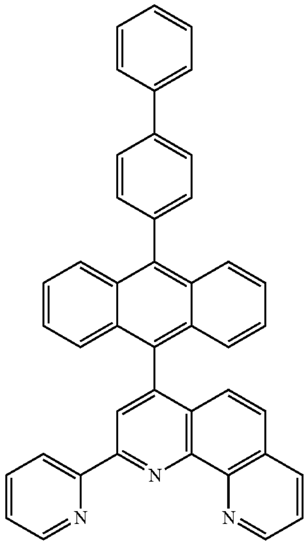

ET35

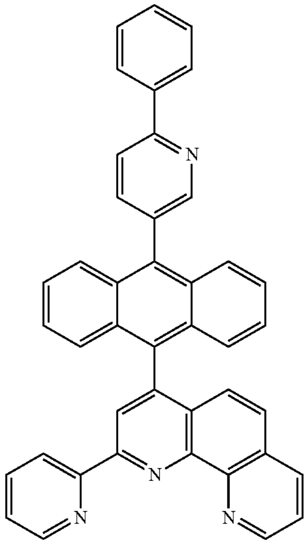

ET36

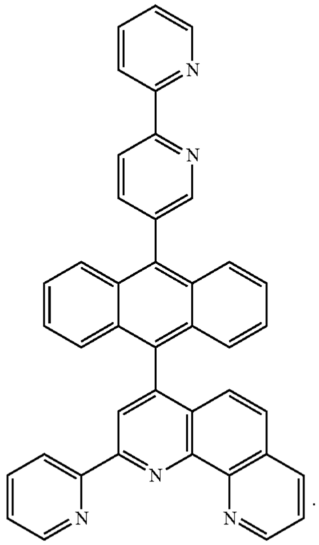

2. The organic compound according to claim 1, wherein the organic compound has a glass transition temperature greater than or equal to 120° C.

3. A display panel, comprising an organic electroluminescent device, wherein the organic electroluminescent device comprises:

a substrate, an anode;

a cathode arranged opposite to the anode;

a first capping layer located at a side of the cathode facing away from the anode; and one or more organic functional layers located between the anode and the cathode, wherein the one or more organic functional layers comprise an electron injection layer, an electron transmission layer, a light-emitting layer, a hole transmission layer, and a second capping layer, and at least one of the electron injection layer, the electron transmission layer, or the light-emitting layer contains the organic compound according to claim 1.

4. The display panel according to claim 3, wherein an energy difference between a LUMO energy level of a material of the electron transmission layer and a LUMO energy level of a material of the light-emitting layer or the electron injection layer is less than 0.2 eV; and an energy of a HOMO energy level of the material of the electron transmission layer is at least 0.3 eV greater than an energy of a HOMO level of the material of the electron injection layer.

5. The display panel according to claim 3, wherein the electron injection layer comprises the organic compound according to claim 1 and a doping metal.

6. The display panel according to claim 5, wherein the doping metal is selected from a group consisting of sodium, potassium, calcium, cesium, ytterbium and combinations thereof.

7. The display panel according to claim 5, wherein the doping metal is doped in the electron injection layer with an amount of from 1% by weight to 5% by weight.

8. The display panel according to claim 5, wherein the doping metal is doped in the electron injection layer with an amount of 3% by weight.

9. A display apparatus, comprising the display panel according to claim 3.

* * * * *